(12) United States Patent        (10) Patent No.:     US 7,885,381 B2
Nagumo et al.                    (45) Date of Patent:     Feb. 8, 2011

(54) METHOD FOR INSPECTING PIPES, AND RADIOGRAPHIC NON-DESTRUCTIVE INSPECTION APPARATUS

(75) Inventors: Yasushi Nagumo, Tokai (JP); Jun Nukaga, Kasama (JP); Hiroshi Kamimura, Hitachi (JP); Noriyuki Sadaoka, Tokai (JP); Satoshi Takemori, Hitachiohta (JP); Kojirou Kodaira, Hitachinaka (JP)

(73) Assignee: Hitachi-GE Nuclear Energy, Ltd., Ibaraki (JP)

( * ) Notice: Subject to any disclaimer, the term of this patent is extended or adjusted under 35 U.S.C. 154(b) by 73 days.

(21) Appl. No.: 12/108,183

(22) Filed: Apr. 23, 2008

(65) Prior Publication Data

US 2008/0267345 A1     Oct. 30, 2008

(30) Foreign Application Priority Data

Apr. 26, 2007  (JP) ............................. 2007-116302
Sep. 27, 2007  (JP) ............................. 2007-250402

(51) Int. Cl.
    G01N 23/04    (2006.01)
(52) U.S. Cl. ........................... 378/59; 378/41
(58) Field of Classification Search ............ 378/4, 378/41, 59
    See application file for complete search history.

(56) References Cited

U.S. PATENT DOCUMENTS

| 5,847,398 | A * | 12/1998 | Shahar et al. ............... 378/149 |
| 2001/0028697 | A1 * | 10/2001 | Nahaliel et al. ............... 378/4 |
| 2002/0181653 | A1 | 12/2002 | Birdwell et al. |
| 2003/0123614 | A1 * | 7/2003 | Silver et al. ............... 378/146 |
| 2004/0165760 | A1 | 8/2004 | Veneruso |
| 2005/0041775 | A1 * | 2/2005 | Batzinger et al. ............. 378/59 |
| 2005/0105693 | A1 * | 5/2005 | Zhao et al. .................. 378/210 |
| 2005/0226375 | A1 * | 10/2005 | Eberhard et al. ............. 378/62 |
| 2007/0019784 | A1 | 1/2007 | Ting |

(Continued)

FOREIGN PATENT DOCUMENTS

JP    3-100405 A    4/1991

(Continued)

OTHER PUBLICATIONS

"Mobile 3D-X-Ray Tomography for Analysis of Planar Defects in Welds By Tomocar", B. Redmer, et al., (2004).

(Continued)

*Primary Examiner*—Chih-Cheng G Kao
(74) *Attorney, Agent, or Firm*—Mattingly & Malur, P.C.

(57) ABSTRACT

The pipe inspection method and apparatus can be used to implement rapid, tomographic inspection of a pipe set up at a narrow location. The pipe inspection method includes: a first step for scanning the pipe by translating a radiation source and radiation detector arranged oppositely to the pipe; a second step for the radiation detector to detect radiation that the radiation source has emitted, at given scanning distance intervals; a third step for creating a transmission image of the pipe, based on a radiation dose that the radiation detector has detected; and a fourth step for constructing a tomogram or stereoscopic image of the pipe, based on the transmission image. Thus, it is possible to provide the pipe inspection method and apparatus that can be used to implement rapid, tomographic inspection of the pipe set up at a narrow location.

9 Claims, 29 Drawing Sheets

U.S. PATENT DOCUMENTS

2008/0073538 A1* 3/2008 Vija et al. ............... 250/363.04
2008/0175456 A1* 7/2008 Ioannou ...................... 382/131

FOREIGN PATENT DOCUMENTS

| JP | 9-161041 | 6/1997 |
| JP | 2000-215304 | 8/2000 |
| JP | 2003-202304 A | 7/2003 |
| JP | 2004-108990 A | 4/2004 |

OTHER PUBLICATIONS

"Pipe Wall Thickness Inspection Apparatus", T. Hamada, et al., vol. 61, No. 6, (2006), pp. 68-71.

* cited by examiner

*FIG.5*
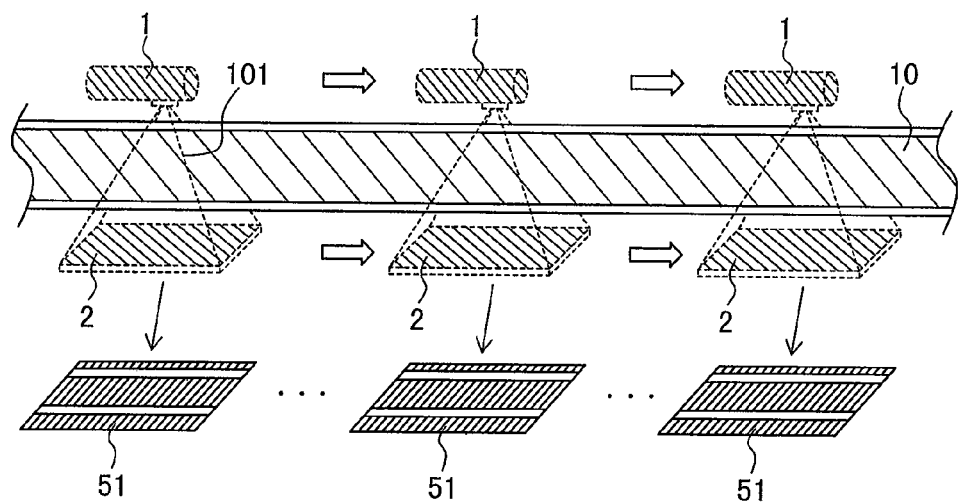
*FIG.6A*  *FIG.6B*  *FIG.6C*
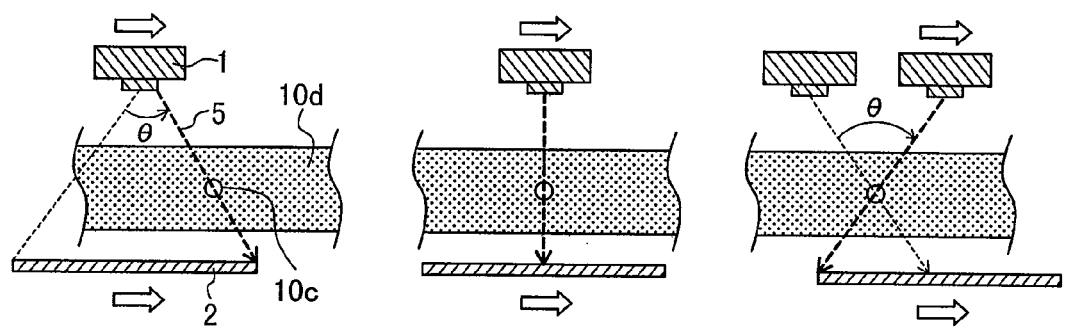

METHOD FOR INSPECTING PIPES, AND RADIOGRAPHIC NON-DESTRUCTIVE INSPECTION APPARATUS

BACKGROUND OF THE INVENTION

1. Field of the Invention

The present invention relates to a method for inspecting pipes, and to a radiographic non-destructive inspection apparatus.

2. Description of the Related Art

Non-Patent Documents 1 and 2 disclose techniques usable as non-destructive inspection methods to visualize and inspect the internal sections of pipeline structures installed at specific locations, such as those set up at nuclear power plants, thermal power plants, chemical plants, and the like.

Non-Patent Document 1: Hamada and Katayama, "Pipe Wall Thickness Inspection Apparatus", Toshiba Review Vol. 61, No. 6, pp. 68-71 (2006)

Non-Patent Document 2: B. Redmer, et. al, "MOBILE 3D X-RAY TOMOGRAPHY FOR ANALYSIS OF PLANAR DEFECTS IN WELDS BY "TOMOCAR", 16th WCNDT proceedings (2004)

SUMMARY OF THE INVENTION

The techniques disclosed in Non-Patent Documents 1 and 2 have the problem that the inspection is time-intensive and thus decreases the inspection efficiency.

Accordingly, an object of the present invention is to improve the inspection efficiency during radiographic non-destructive inspection of, for example, pipes set up at plants and the like.

A method of inspecting a pipe according to the present invention comprises: a first step in which to scan the pipe by translating a radiation source and radiation detector disposed oppositely to the pipe, a second step in which the radiation detector detects at given scanning distance intervals a beam of radiation emitted from the radiation source, a third step to create a transmission image of the pipe, pursuant to a radiation level detected by the radiation detector, and a fourth step in which to construct a tomogram or stereoscopic image of the pipe in accordance with the transmission image.

An apparatus of inspecting a pipe according to the present invention comprises: a supporting device disposed such that a radiation source and a radiation detector face each other across the pipe, a driving device that translates the radiation source and the radiation detector via the supporting device in order to conduct scans, a radiation detector controller that acquires transmission data from the radiation detector at given scanning distance intervals, and an image reconstruction arithmetic device that reconstructs a two-dimensional tomogram or three-dimensional stereoscopic image based on the transmission data.

Accordingly, the present invention makes it possible to improve the inspection efficiency during radiographic non-destructive inspection of, for example, pipes set up at plants and the like.

BRIEF DESCRIPTION OF THE DRAWINGS

FIG. 5 is a diagram that describes a method of acquiring transmission data using a radiographic imaging apparatus in an embodiment of the present invention;

FIGS. 6A to 6C are diagrams that describe an acquisition range of the transmission data used in image reconstruction arithmetic operations;

DETAILED DESCRIPTION OF THE PREFERRED EMBODIMENTS

Figure 1:
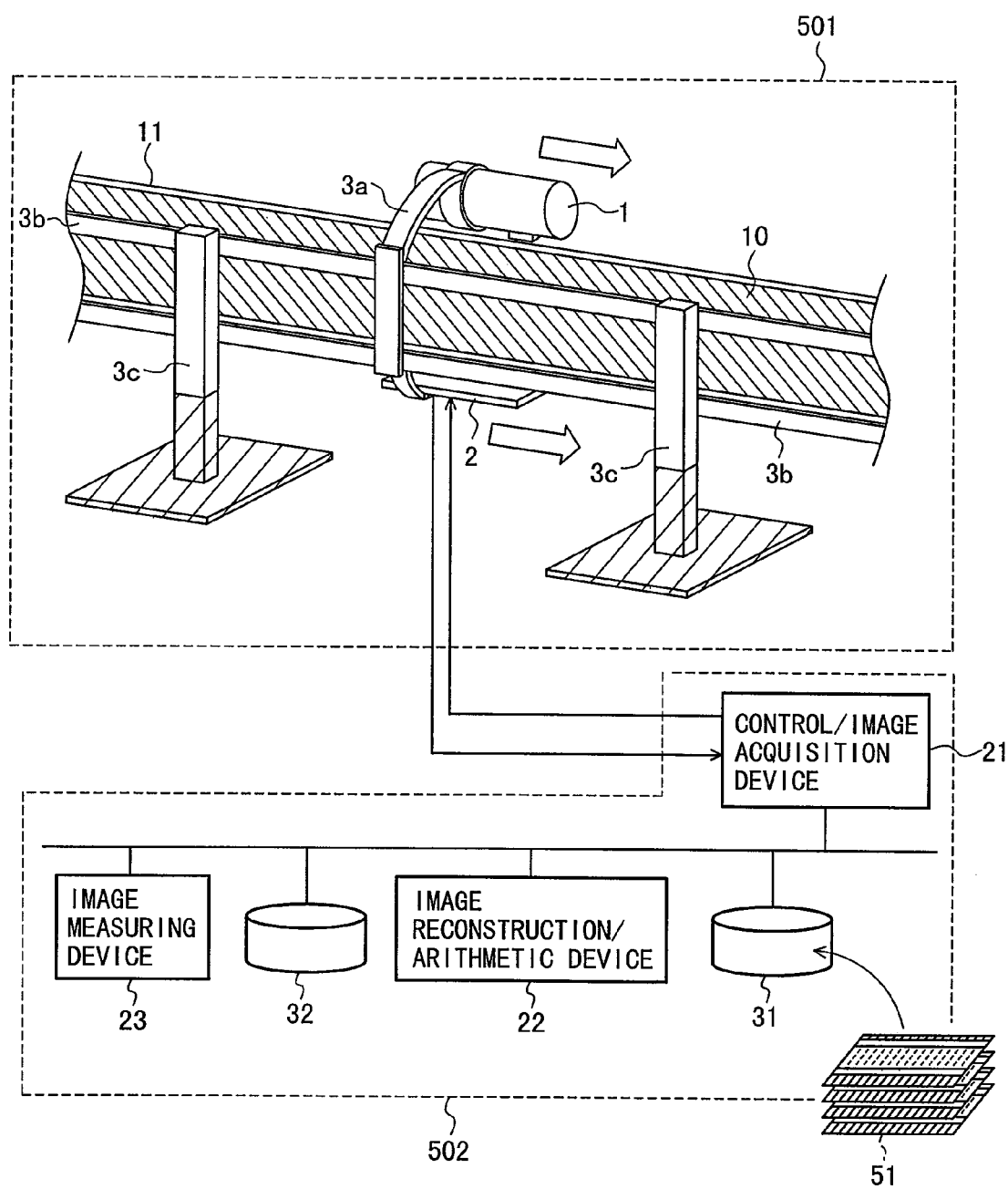
FIG. 1 is a diagram that describes a configuration of a first embodiment of the present invention.

Non-destructive inspection methods for visualizing and inspecting the internal sections of the structures installed at specific locations, such as those of the pipelines set up at nuclear power plants, thermal power plants, chemical plants, and the like, include radiographic testing (RT) that uses X-rays, gamma-rays, or other radiation. The RT method is used to acquire two-dimensional transmission images of a structure to be inspected (hereinafter, this structure is called the "subject"), by emitting radiation from a radiation source to the subject and measuring the radiation with a radiation detector installed at the opposite side of the radiation source across the subject. During the inspection with RT, acquired transmission images are used for purposes such as confirming the status of the subject interior and measuring its dimensions.

An apparatus that uses RT to inspect plant pipes for reduced wall thickness is disclosed in [Non-Patent Document 1]. The apparatus described therein scans the plant pipes by using a radiation source and highly sensitive image intensifier (radiation detector) installed on a supporting mechanism called a C-arm. Transmission images of the pipes are acquired and decreases in wall thickness are measured from the transmission images.

Computed tomography (CT) is available as another non-destructive inspection method that uses radiation. A general X-ray CT apparatus for industrial applications has a fixed X-ray source and radiation detector, and rotates a subject installed on a disc present between the X-ray generator and the radiation detector. This type of CT apparatus acquires transmission images from all circumferential directions of the subject by radiation exposure while rotating the subject, and obtains tomograms by image reconstruction. The difference from RT-based transmission imaging is that three-dimensional stereoscopic images of the subject interior can be obtained. This allows the acquisition of further detailed position information on the internal structure of the subject.

In [Non-Patent Document 2], an apparatus that inspects welded pipe seams is disclosed as a radiation CT apparatus for non-destructive inspection of pipes. This CT apparatus is based on a radiographic method called "laminography". Laminography is a radiographic method that allows the acquisition of tomograms parallel to the moving directions of a radiation source and a radiation detector, both installed so as to face each other across a subject, by causing the relative motions of both in parallel and in reverse directions with respect to each other. The depth of the laminographic plane as viewed from the radiation source can be varied by changing the moving distance of the radiation detector with respect to that of the radiation source. The apparatus in [Non-Patent Document 2] is based on the radiographic principles of laminography, and executes radiography using a compact X-ray source and radiation detector installed on a pipe-mounted scanner. Radiography is executed by moving the X-ray source in the circumferential direction or major-axis direction of the pipe with the radiation detector remaining fixed.

The above techniques, however, have had the following respective problems:

Firstly, RT has the problem that any thinned-down sections of the pipe which is the subject look differently according to the particular radiographing direction. This is because, since the subject that is actually of three-dimensional construction is radiographed as a two-dimensional transmission image, depth-wise information in the radiographing direction is superimposed. For this reason, RT has required radiographing the subject from a plurality of directions to search for a radiographing direction that allows the thinned-down sections of the pipe to be observed, and it has usually taken several minutes to several tens of minutes to perform these operations.

Secondly, CT requires rotating the subject or rotating the radiation source and the radiation detector about the subject. However, it is impossible to rotate the pipes set up at a plant. In addition, the surroundings of the pipes are commonly narrow and spatially confined and there is usually no room for rotating the radiation source and the radiation detector about the pipes. That is to say, there has been the problem that conventional CT scanning cannot be applied to the structures set up at narrow and confined locations, such as the pipes laid out at nuclear power plants, thermal power plants, chemical plants, and the like.

Thirdly, tomographic scanning of a pipe by laminography needs to be executed using a fixed radiation detector, so the imaging zone during one scanning operation depends upon the detector size of the radiation detector. The size of the radiation detector is several tens of centimeters. Imaging the entire pipe as long as several meters requires a very great deal of time. Additionally, scanning with the radiation source or the radiation detector is complicated and thus requires time-consuming alignment. Hence, inspection efficiency decreases.

Laminography has another problem in that generating a plurality of tomograms or three-dimensional stereoscopic images by image reconstruction increases a calculation time and a data volume very significantly, compared with RT-based imaging. For a target pipe inspection region as long as several meters, generating tomograms or three-dimensional stereoscopic images of the entire inspection region could lead to very great increases in both calculation time and data volume, and is thus likely to deteriorate inspection efficiency.

A conceivable method to avoid the problems present in Non-Patent Documents 1 and 2 is by executing computed tomography(CT) scans after a transmission image of the pipe has been acquired over the entire length thereof to identify a place of inspection. This method is actually used in medical X-ray CT scanners. In this method, however, transmission imaging for identifying the inspection place and CT scanning become separate processes. Since transmission image data and CT scanning data for image reconstruction also become separate data, the foregoing problems associated with an inspection time and a data capacity remain to be solved.

In particular, when pipe inspection is to occur during routine inspection of a nuclear power plant, since the plant is difficult to shut down for a long term, it is required to improve inspection efficiency by reducing the time required for the pipe inspection.

Hereunder, embodiments of the present invention are described using drawings. In the description, a pipe set up at an electric power plant or the like is used by way of example as a subject of inspection.

First Embodiment

An embodiment of the present invention is shown in FIG. 1. This figure illustrates an apparatus that implements a radiation tomographic method of the present invention. In addition, FIG. 1 assumes a major-axis direction of a pipe as a direction in which a radiation source and a radiation detector are moved for scanning. Although the radiation source using an X-ray tube is shown, a gamma-ray source can, of course, be used as an alternative. Furthermore, a two-dimensional radiation detector is assumed as the above radiation detector. In addition to a detector that converts into photoelectron form a beam of light emitted from an input phosphor screen provided on an incident plane of radiation, and focuses the photoelectron to output an optical image, major types of two-dimensional radiation detectors include a flat-panel detector (FPD), which is a radiation detector in which radiation detection elements measuring 0.1 to 0.3 mm square are densely arranged in grid form. In general, a FPD is easily applicable, even at spatially confined locations, since a depth of the detector is smaller than that of the detector that outputs an optical image by focusing the photoelectron. The present embodiment is therefore described assuming that the two-dimensional radiation detector is a FPD. Instead of this configuration, however, the apparatus configuration can use the detector that outputs an optical image by focusing the photoelectron. Moreover, a conical radiation beam is emitted as a cone beam 101 from the radiation source 1 to the two-dimensional radiation detector 2.

The radiation tomographic apparatus according to the present embodiment includes an imaging system 501 for acquiring transmission data, and a control and arithmetic system 502 which controls the imaging system 501 and executes image reconstruction arithmetic operation, and the like, thereof.

The imaging system 501 has a guide rail 3b supported by support legs 3c and disposed along the pipe 10, and a supporting device 3a mounted on the guide rail 3b. The supporting device 3a supports the radiation source 1 and two-dimensional radiation detector 2 arranged opposedly to each other across the pipe 10 covered with a heat-insulating material 11. Hereinafter, the supporting device 3a, the guide rail 3b, and the support legs 3c are collectively called a scanner 503. FIG. 1 shows the way the imaging system 501 acquires images while moving from the left of the drawing to the right thereof, in a major-axis direction of the pipe 10. The scanner 503 here has a driving device that actuates the scanner along the surface of the guide rail laid out on a side of each support leg 3c set up on a floor. A compact scanner may, for example, be mounted directly on lagging of the heat-insulating material 11, or if the heat-insulating material is absent, on the pipe 10. For calibration of the two-dimensional radiation detector 2, radiation is emitted without a subject before imaging is started. On the basis of the calibration data obtained at that time, the radiation detector 2 outputs signal data equivalent to the intensity of the radiation.

The control and arithmetic system 502 has a control/image acquisition device 21, a transmission image storage device 31, an image reconstruction arithmetic device 22, and a reconstruction arithmetic result storage device 32. The control/image acquisition device 21 controls the scanner 503, the radiation source 1, and the two-dimensional radiation detector 2, and acquires a plurality of transmission images 51 that are signal values equivalent to the radiation intensity which has been acquired by the two-dimensional radiation detector 2. The acquired transmission images 51 are stored into the transmission image storage device 31. The image reconstruction arithmetic device 22 loads (reads in) a plurality of transmission images 51 and reconstructs two-dimensional tomograms or three-dimensional stereoscopic images of the subject. The reconstructed two-dimensional tomograms or three-dimensional stereoscopic images of the subject are stored into the reconstruction arithmetic result storage device 32. An image-measuring device 23 with image-measuring software (or the like) installed therein to implement image measurement which uses two-dimensional tomograms or three-dimensional stereoscopic images is shown in FIG. 1 to allow for convenience of a user.

Figure 2:
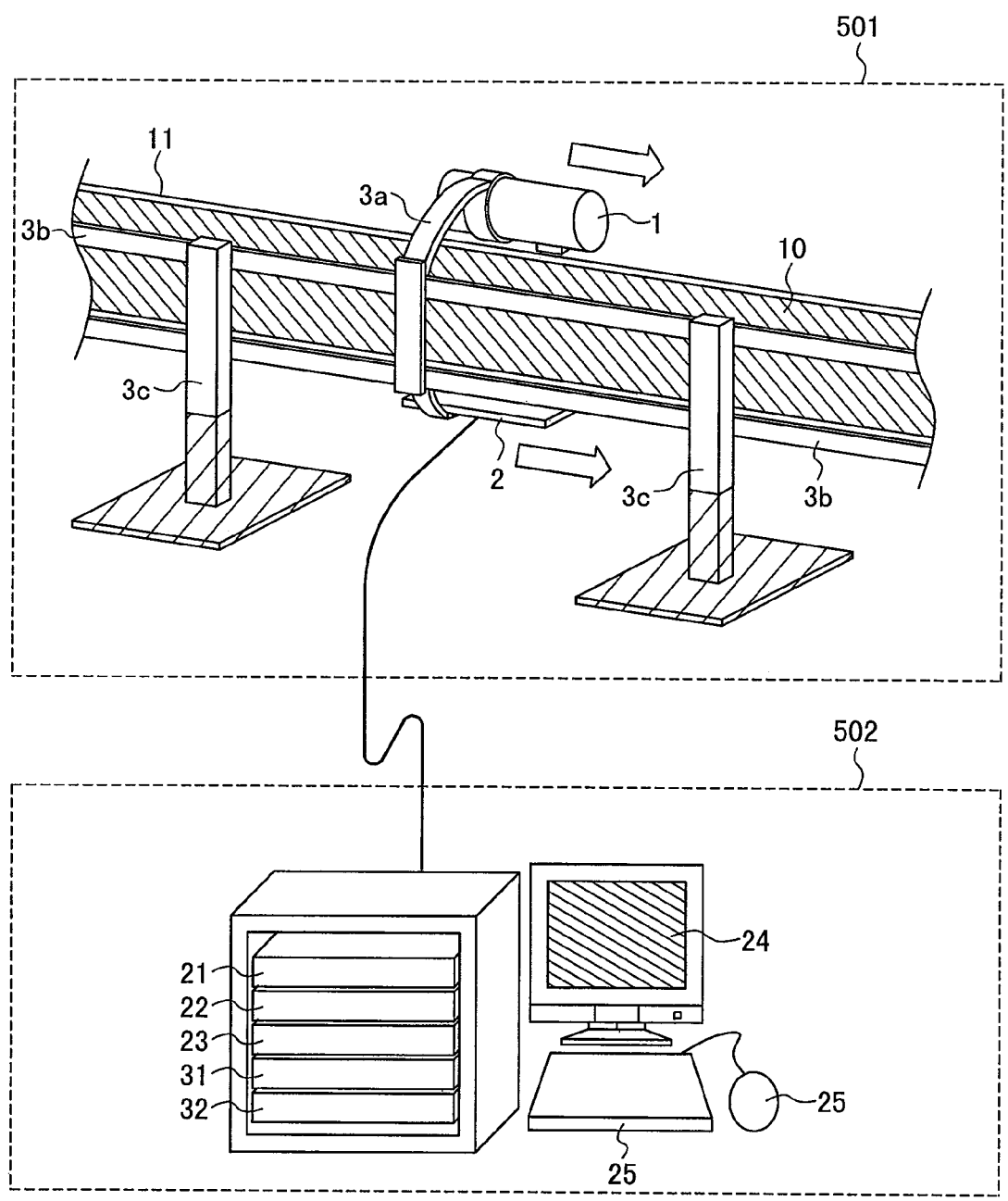
FIG. 2 is a diagram that describes a more specific example of an embodiment of the present invention.

FIG. 2 shows an example of an apparatus in which the imaging system 501 and the control and arithmetic system 502 are connected. In FIG. 2, an input device 25 that accepts operator entry, and a display device 24 for image confirmation are connected to the apparatus.

Figure 3:
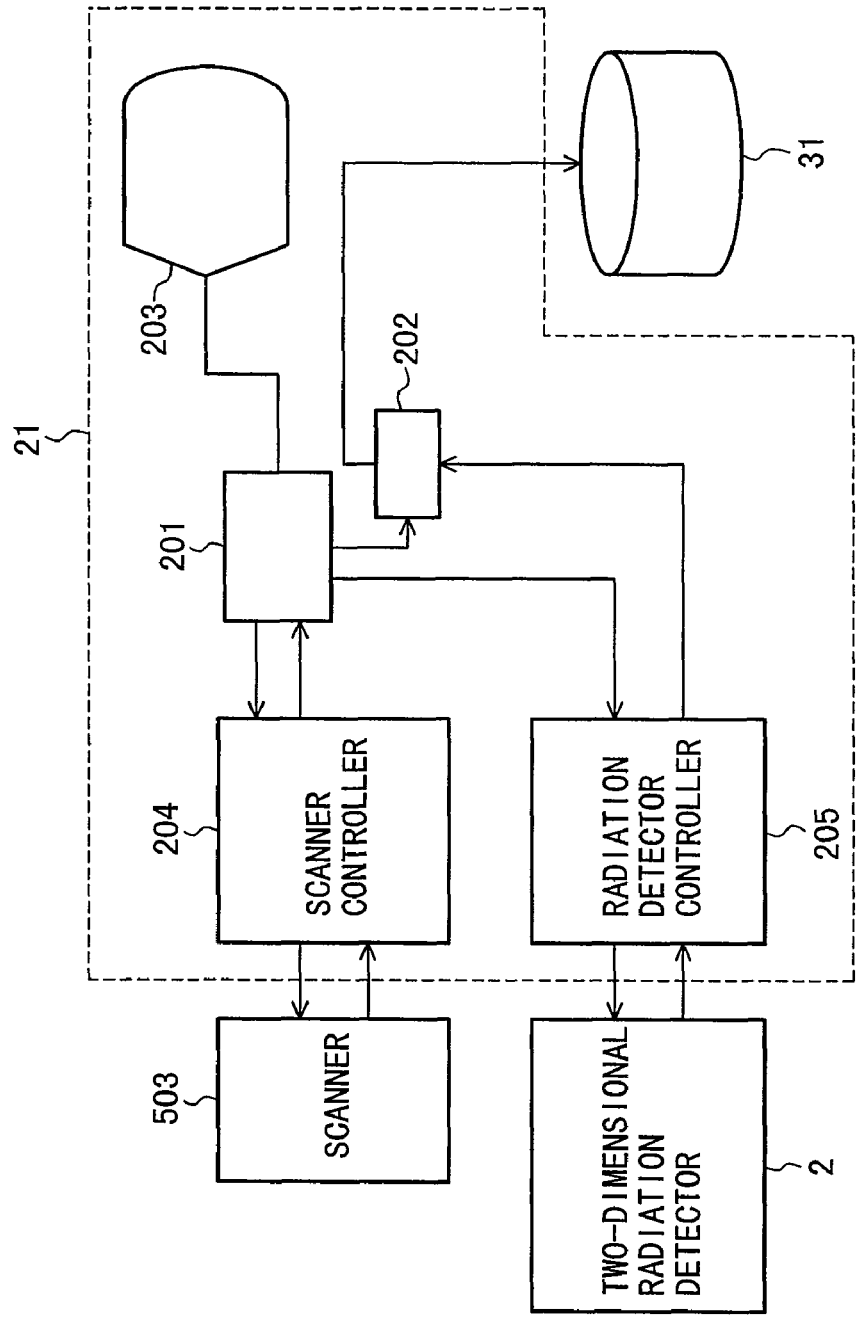
FIG. 3 is a diagram that describes a configuration of a control/image acquisition device in an embodiment of the present invention.

FIG. 3 shows a block diagram of the control/image acquisition device 21. The control/image acquisition device 21 includes a central control device 201, an image acquisition device 202, a scanner controller 204, a radiation detector controller 205, and a display/input device 203. The central control device 201 exchanges controller commands to control the entire apparatus. The image acquisition device 202 acquires the plurality of transmission images 51 that the two-dimensional radiation detector 2 has obtained. The scanner controller 204 exchanges commands with the central control device 201 and operates the scanner 503. The radiation detector controller 205 exchanges commands with the central control device 201, controls the two-dimensional radiation detector 2, and transmits the plurality of transmission images 51 to the image acquisition device 202. The display/input device 203 is used for the user to enter control parameters, and displays control results as well as the parameters.

The plurality of transmission images 51 that the image acquisition device 202 has acquired are stored into the transmission image storage device 31. Although shown as constituent elements of the control/image acquisition device 21 in FIG. 3, the scanner controller 204 and the radiation detector controller 205 can be included in the imaging system 501 instead.

Figure 4:
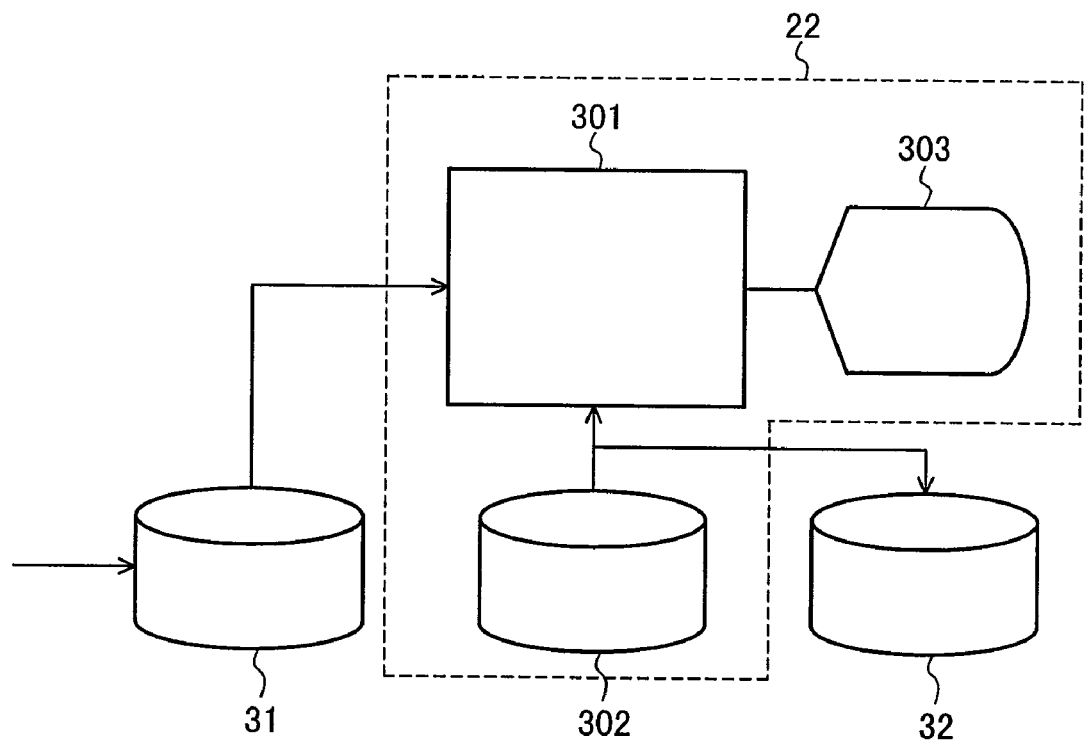
FIG. 4 is a diagram that describes a configuration of an image reconstruction arithmetic device in an embodiment of the present invention.

FIG. 4 shows a block diagram of the image reconstruction arithmetic device 22. The image reconstruction arithmetic device 22 includes a central arithmetic device 301, a program storage device 302, and a display/input device 303. The central arithmetic device 301 loads the plurality of transmission images 51 from the transmission image storage device 31 and executes an image reconstruction arithmetic process. The program storage device 302 saves image reconstruction arithmetic programs. The display/input device 303 is used for the user to enter arithmetic parameters, and displays arithmetic results and images as well as the parameters. Image reconstruction arithmetic results on two-dimensional tomograms, three-dimensional stereoscopic images, and the like, are stored into the reconstruction arithmetic result storage device 32.

FIG. 5 is a diagram that explains a method of acquiring transmission images with this radiation tomographic apparatus. The radiation source 1 and two-dimensional radiation detector 2 arranged opposedly to each other across the pipe 10 covered with the heat-insulating material 11 are synchronously translated in the major-axis direction of the pipe 10 at a constant velocity by the scanner controller 204 to scan the pipe. More specifically, the scanner controller 204 transmits a command to the scanner 503 (not shown in FIG. 5) to allow scanning by the scanner 503. A scanning time can be reduced since the radiation source 1 and the two-dimensional radiation detector 2 need only to be translated in one direction (the major-axis direction of the pipe 10). In addition, since the two-dimensional radiation detector 2 moves together with the radiation source 1, an imaging time of the entire pipe can be reduced, irrespective of a size of the two-dimensional radiation detector 2.

During scanning, radiation is constantly emitted from the radiation source 1. That is to say, cone beams 101 are emitted therefrom. Also, the radiation detector controller 205 transmits a radiation detection command to the two-dimensional radiation detector 2 at definite time intervals. Each time the two-dimensional radiation detector 2 receives the command during scanning at the constant velocity, the radiation detector 2 detects the radiation that has penetrated the pipe 10 and the heat-insulating material 11, and outputs one transmission image as a two-dimensional image with each detecting operation. This two-dimensional image is acquired by the image acquisition device 202.

If the moving velocity of the scanner 503 is expressed as "v" (m/s), and a detection time interval of the two-dimensional radiation detector 2, as "•t" (sec), a distance "•u" through which the scanner 503 moves during output of one transmission image is calculated using expression (1).

$$•u = v•t \quad \text{(Expression 1)}$$

The moving distance "•u" of the scanner 503 is usually determined allowing for resolution and/or other factors of a reconstructed image finally obtained, such as a two-dimensional tomogram or a three-dimensional stereoscopic image. For output of a high-resolution image, for instance, it is conceivable that "•u" is made equal to a detection element arrangement spacing (up to about 0.3 mm) of the two-dimensional radiation detector 2. Also, "•t" is determined by a data output time interval that is among specifications of the two-dimensional radiation detector 2. For FPD, for instance, since a large majority of commercially available devices output a maximum of 30 frames (images) within one second, a shorter detection time interval is "•t=1/30" (sec). From these facts, the moving velocity "v" of the scanner 503 is, in fact, determined on the basis of the moving distance "•u" thereof and the detection time interval "•t" of the two-dimensional radiation detector 2, pursuant to expression (2).

$$v = •u/•t \quad \text{(Expression 2)}$$

When the pipe 10 is scanned over a length of one meter in the major-axis direction thereof, N that is the number of transmission images output during the scan is calculated per expression (3).

$$N = 1/(v•t) = 1/•u \quad \text{(Expression 3)}$$

For high-resolution output of reconstructed images, if •u=0.2×10⁻³ (m), the number of transmission images, N, is 5,000. This value of N can be reduced if the reconstructed-image output at a lower resolution is sufficient.

A way to create a two-dimensional tomogram or three-dimensional stereoscopic image from the plurality of transmission images 51 using the image reconstruction arithmetic device 22 is next discussed below. FIGS. 6A to 6B show a transmission image acquisition range required for image reconstruction. For simplicity, the figure shows two-dimensional imaging. This two-dimensional imaging concept is expanded to implement three-dimensional imaging. A case in which the radiation source 1 and the two-dimensional radiation detector 2 are translated from left to right for scanning, as in FIGS. 6A to 6C, is now considered. Also, a plate-like object 10d is considered as the subject in this case, and attention is focused upon an internal point 10c of the object 10d.

Radiation 5 that penetrates the internal point 10c during translational scanning starts from the direction shown in FIG. 6A, and after penetrating in the direction shown in FIG. 6B, ends in the direction shown in FIG. 6C. If an emission angle of the radiation 5 is taken as •, an angle range of the radiation 5 penetrating the internal point 10c during the translational scans also becomes •. In general, to create a tomogram by CT image reconstruction, radiation needs to be made to penetrate in an angle range from 180° C. to 360° C. with respect to the subject of inspection. In the imaging system 501, however, the penetrating angle of the radiation is •, and this value determined by an radiation angle of the radiation source 1 or by a size of a detection surface of the two-dimensional radiation detector 2 ranges from about 40° C. to 60° C. Image reconstruction under these conditions needs to be conducted in a limited projection angle state (this reconstruction is called "limited-angle image reconstruction").

A large number of limited-angle image reconstruction techniques have heretofore been proposed. These techniques range over a variety, including, for example, one that utilizes a previously known subject shape as prior information, and one in which missing transmission data from the projection angle direction is estimated from or interpolated using acquired data relating to penetration from other projection angle directions. The principles of image reconstruction are described below taking digital tomosynthesis (DTS) as an example of such a technique. Of course, other limited-angle image reconstruction techniques are applicable instead.

Figure 7:
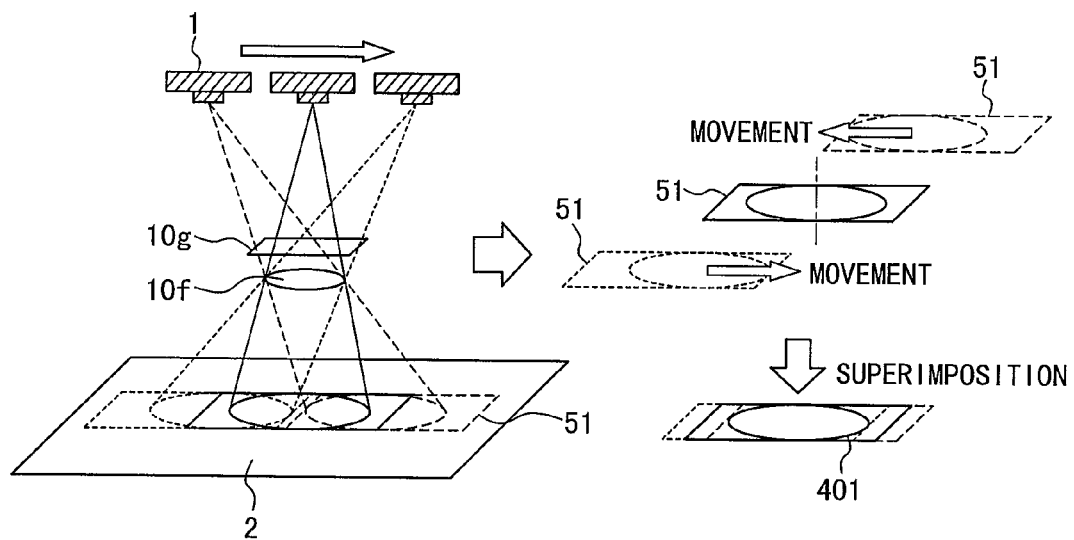
FIG. 7 is a diagram that describes principles of image reconstruction in an example of an image reconstruction technique.

The principles of image reconstruction based on the DTS method are shown in FIG. 7. For simplicity, assume a case in which only the radiation source 1 is translated and the two-dimensional radiation detector 2 is fixed. Also, assume that a circular subject 10f without thickness and a rectangular subject 10g without thickness are used as the subjects of inspection, and that both subjects are arranged perpendicularly to a directional axis extending from the radiation source 1 and heading for the two-dimensional radiation detector 2, and in parallel to the radiation detector 2. Additionally, assume that the circular subject 10f and the rectangular subject 10g differ in distance from the radiation source 1. When the subjects 10f, 10g are imaged, the transmission images 51 as shown in FIG. 7 are obtained for each translating position of the radiation source 1. When tomographic planes including the circular subject 10f are reconstructed from the above-obtained transmission images 51, these transmission images are moved so that projected portions of the circular subject 10f on each transmission image are superimposed as shown, and then, all entire transmission images are superimposed as shown. This process forms a clear, circular image. A moving distance of each transmission image is determined by that of the radiation source 1 existing during the acquisition of each transmission image, a distance between the radiation source 1 and the tomographic planes including the circular subject 10f, and a distance between the two-dimensional radiation detector 2 and the tomographic planes including the circular subject 10f. Projected portions of the subject 10g on the transmission images appear as a blurred image because of the above movement and superimposition of each transmission image. This causes a difference in contrast between the circular subject 10f and the rectangular subject 10g, thus making it possible to reconstruct two-dimensional tomograms 401 of the circular subject 10f.

Figure 8:
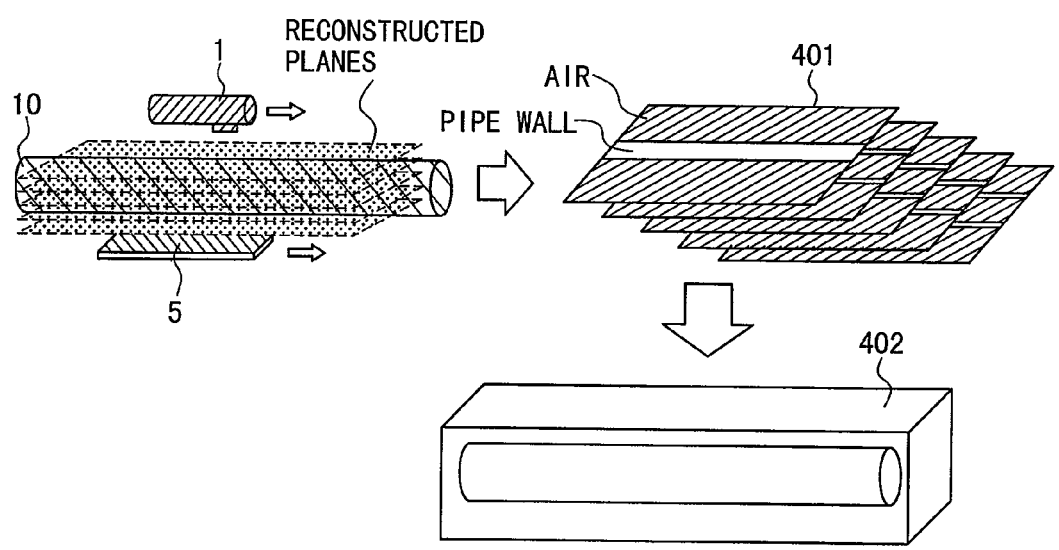
FIG. 8 is a diagram that describes an example of applying a radiographic imaging apparatus and an image reconstruction arithmetic operation to a pipe.

An example of applying the imaging system 501 and such a limited-angle reconstruction imaging technique as the DTS method to pipe imaging is shown in FIG. 8. In this example, two-dimensional tomograms 401 are reconstructed between the radiation source 1 and the two-dimensional radiation detector 2, as tomographic planes each having a normal vector parallel to the axis extending from the radiation source 1 and heading for the two-dimensional radiation detector 2. Piling up these two-dimensional tomograms 401 makes a three-dimensional stereoscopic image 402 constructible.

As set forth above, in the present embodiment, the scanning time can be reduced significantly since two-dimensional tomograms or three-dimensional stereoscopic images can be constructed using the transmission images obtained by scanning the pipe in one direction (major-axis direction). In addition, since transmission images of the pipe can be acquired while moving the radiation detector, tomographic imaging of the pipes set up at a narrow location is possible in a short time, irrespective of the size of the radiation detector.

Figure 9:
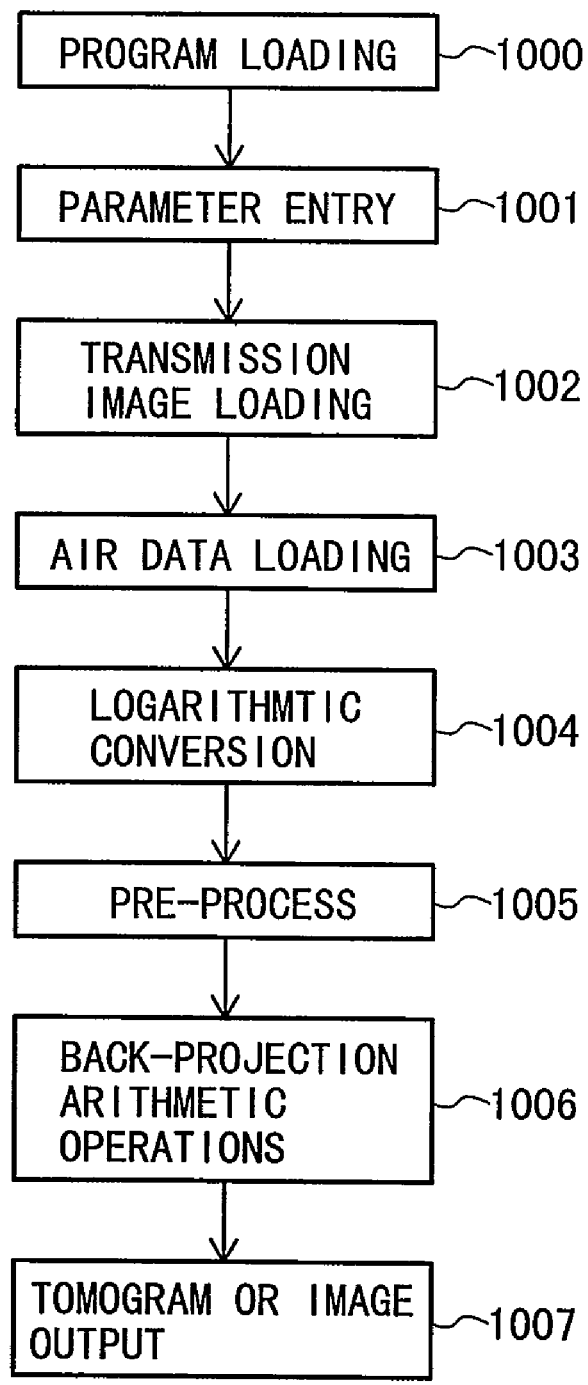
FIG. 9 is a flow diagram of the image reconstruction arithmetic process.

A process flow of image reconstruction arithmetic operations is shown in FIG. 9.

First, the central arithmetic device 301 executes a program-loading process 1000 that loads an image reconstruction arithmetic program from the program storage device 302. After this, an arithmetic parameter entry process 1001 is executed to allow the operator to enter an input data name and other arithmetic parameters from the display/input device 303. Next, a transmission image loading process 1002 that uses the entered arithmetic parameters to load the transmission images 51 which the imaging system 501 has acquired from the transmission image storage device 31, and an air data loading process 1003 that loads air data 52 are executed on the basis of the entered arithmetic parameters. The air data refers to data acquired without a subject, that is, unattenuated radiation intensity data. This data is used in the following process. Next, a logarithmic conversion process 1004 is executed. The logarithmic conversion process occurs to conduct a logarithmic conversion of a ratio between unattenuated radiation intensity and the radiation intensity attenuated during penetration through the subject, and the logarithmic conversion is represented using expression (4).

$$\ln\left(\frac{I_{ou,v}}{I_{u,v}}\right) = \int \mu dt \qquad \text{(Expression 4)}$$

where "$I_{ou,v}$" denotes the unattenuated radiation intensity detected by the radiation detection elements at a position (u, v) on the two-dimensional radiation detector 2, and "$I_{u,v}$" denotes the attenuated radiation intensity detected at the same position. Also, "•" denotes a linear attenuation coefficient depending on the kind of material of the subject or on radiation energy, and "t" denotes a penetration path of the radiation. The image reconstruction arithmetic process is conducted to obtain a spatial distribution of "•" with a left side of expression (4) as an input value. The image reconstruction arithmetic process is followed by a pre-process 1005. Corrections for variations in characteristics and quality between the detector elements, corrections for defects in each of the detector elements, device-dependent corrections, and other corrections are conducted in the pre-process 1005. Depending on a particular situation, the pre-process 1005 may precede the logarithmic conversion process 1004.

After the above processes, a back-projection arithmetic process 1006 is executed. The back-projection arithmetic process provides mapping (back-projection) of corrected and converted data onto a two-dimensional or three-dimensional space. This process corresponds to the movement and superimposition of transmission images in the DTS method described above. Two-dimensional tomograms or three-dimensional stereoscopic images are eventually reconstructed by the back-projection arithmetic process. Reconstructed arithmetic data is stored into the reconstruction arithmetic result storage device 32.

Although an example of using all the plurality of transmission images 51 obtained during one scan has been described above, an area in which a two-dimensional tomogram 401 or a three-dimensional stereoscopic image 402 is to be output may be selected by the user according to a particular purpose and only the selected area may be subjected to image reconstruction.

Arithmetic results on the above image reconstruction are output as either the plurality of two-dimensional tomograms 401 that are different in depth when viewed from the radiation source 1, or a three-dimensional stereoscopic image 402 representing a three-dimensional stereoscopic shape called voxel data. Alternatively, a three-dimensional stereoscopic image 402 can be constructed by stacking a plurality of two-dimensional tomograms 401 of different depths in the image measuring device 23 according to particular needs of the user.

In addition, although an example of moving the scanner 503 continuously at a constant velocity during imaging has been described above, the scanner 503 can be made to repeat a 'walk-through' operational sequence of "moving through •u -> stopping -> imaging for a time of •t and output of transmission images 51 -> moving through •u -> . . . " during imaging. In this case, since the scanner 503 stops during imaging, an overall imaging time increases, but there is an advantage in that clearer transmission images 51 or two-dimensional tomograms 401 or three-dimensional stereoscopic images 402 can be obtained.

Figure 10:
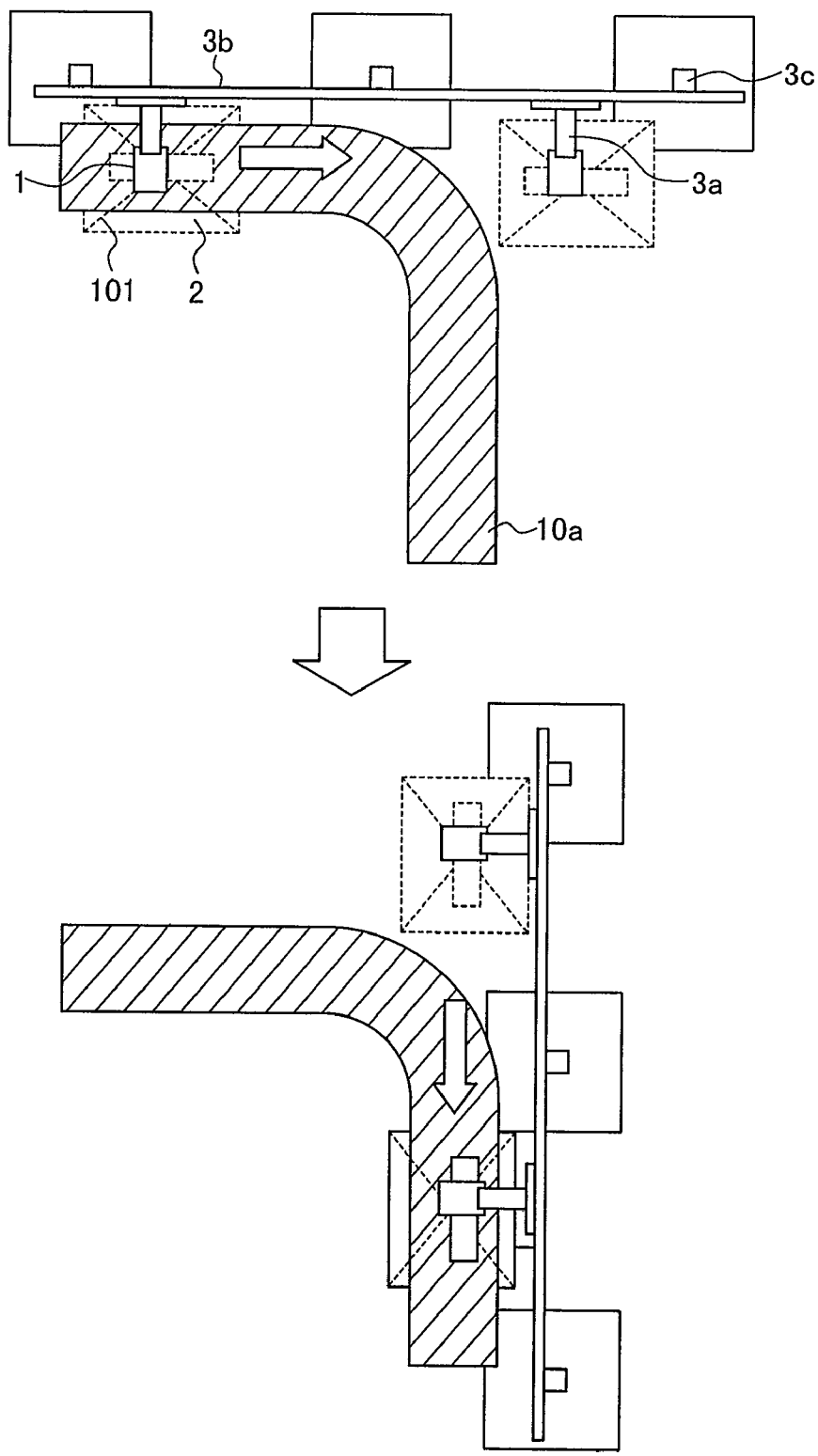
FIG. 10 is a diagram that describes an example in which an apparatus that is an embodiment of the present invention is applied to a bent pipe.

FIG. 10 shows an example in which the apparatus of the present invention is applied to a bent pipe 10a, one form of pipe 10 with a bend. The pipe 10a when viewed from above of the apparatus is shown in FIG. 10. As shown, the apparatus starts rectilinear scanning of the bent pipe 10a in immediate front of the bend thereof. After moving past the bend, the apparatus stops scanning, then changes in direction, and starts scanning along the major axis of the pipe, towards a distal end of the bend. Scanning in this way also makes tomographic imaging of the bent pipe 10a possible.

Figure 11:
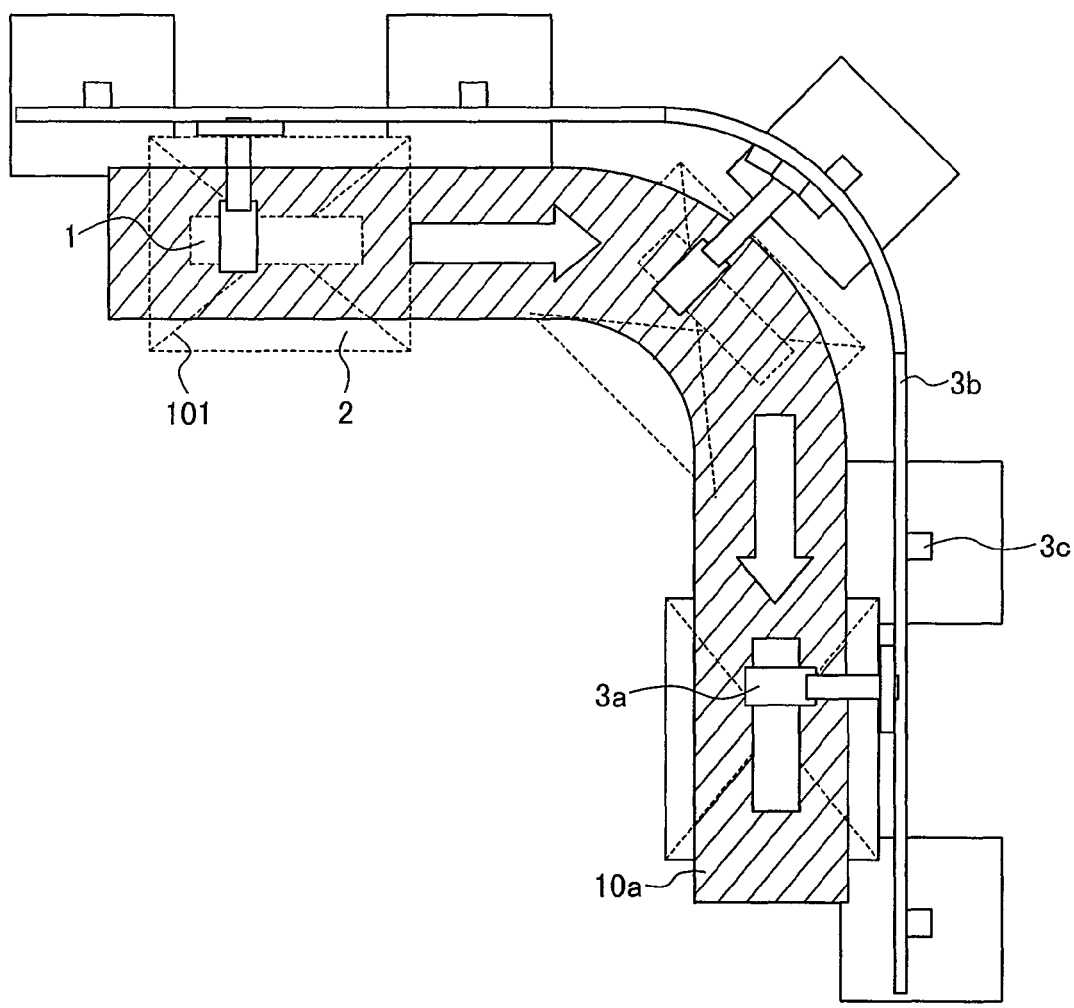
FIG. 11 is a diagram that describes another example in which an apparatus that is an embodiment of the present invention is applied to a bent pipe.

FIG. 11 shows an example of applying another scanning method to tomographic imaging of the bent pipe 10a. In this example, the bent pipe 10a when viewed from above of the apparatus is also shown. In this scanning method, the apparatus starts rectilinear scanning of the bent pipe 10a in immediate front of the bend thereof, as in FIG. 10. This method differs from that of FIG. 10 in that the guide rail 3b is set up along the pipe. As a result, the apparatus changes in scanning direction at the bend and then starts scanning along the major axis of the pipe, towards the distal end of the bend. Scanning in this way also makes tomographic imaging of the bent pipe 10a possible.

Figure 12:
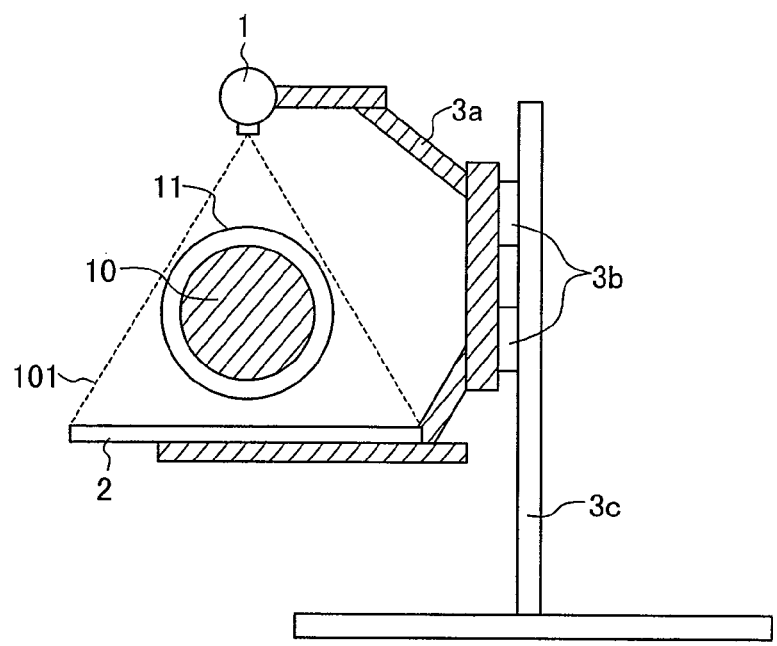
FIG. 12 is a diagram that describes how an apparatus that is an embodiment of the present invention looks when viewed from different directions.
Figure 13:
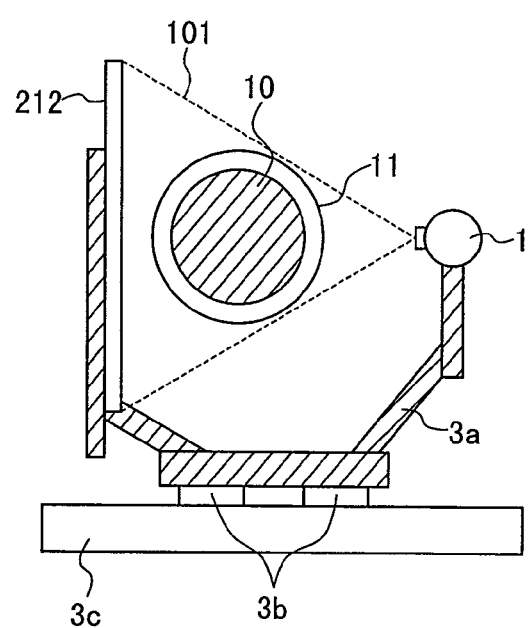
FIG. 13 is a diagram that describes a case in which devices are installed in different directions in an embodiment of the present invention.

The imaging system 501 in the present embodiment is shown in cross-sectional view, inclusive of a C-arm, in FIGS. 12 and 13. In the present embodiment, the radiation source 1 and the two-dimensional radiation detector 2 are respectively arranged above and below the pipe 10. These devices may be arranged at left and right sides of the pipe 10, as shown in FIG. 13. If the radiation source 1 and the two-dimensional radiation detector 2 can be arranged facing each other across the pipe 10, the two devices can also be arranged to face, although not shown, in any direction other than vertically or horizontally with respect to the pipe 10.

Second Embodiment

Figure 14:
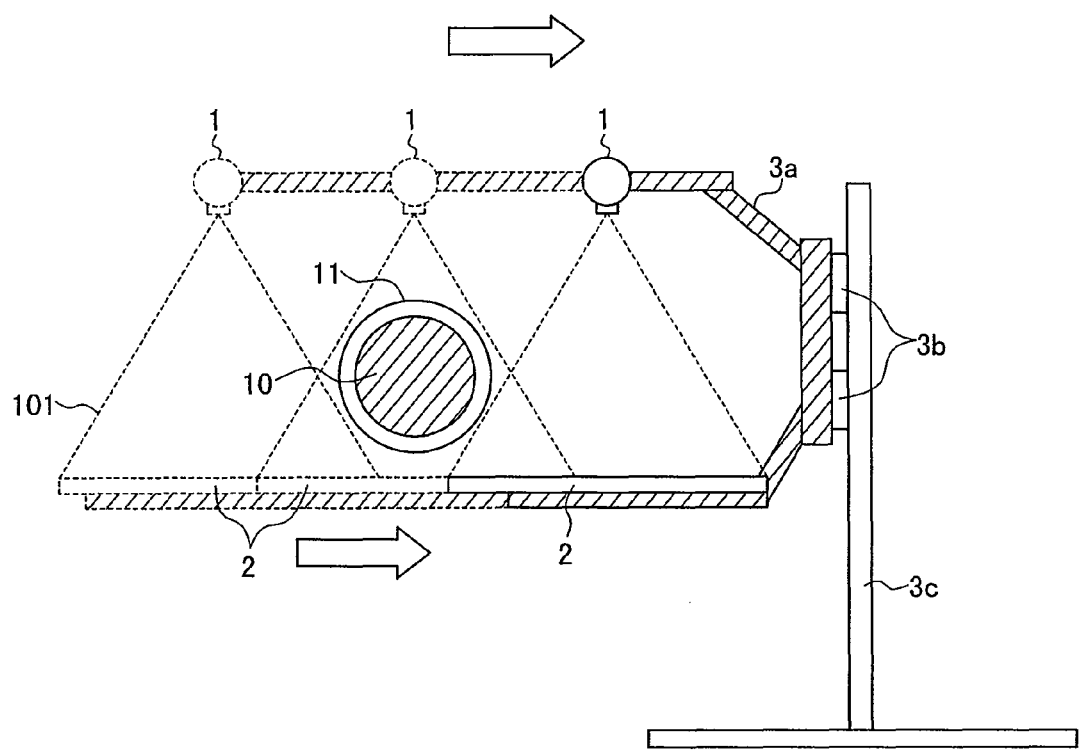
FIG. 14 is a diagram that describes a configuration of a second embodiment of the present invention.

Another embodiment of the present invention is shown in FIG. 14. This figure shows an apparatus that acquires tomograms of the pipe 10 by scanning the pipe in a direction orthogonal to the major-axis direction thereof. In this figure, a radiation source 1 and a two-dimensional radiation detector 2 move so that the pipe 10 is scanned from left to right. Scanning is started from a position at which a right end of a cone beam 101 emitted from the radiation source 1 comes into contact with a heat-insulating material 11 covering the pipe 10, and the scanning operation is finished at where a left end of the cone beam 101 comes into contact with the heat-insulating material 11. A moving velocity of the above two devices during scanning is determined by expression (2), as in the first embodiment. Such scanning can be implemented by providing a supporting device 3a adapted to include an extend/retract unit so that a section for mounting and supporting the radiation source 1, and a section for mounting and supporting the two-dimensional radiation detector 2 synchronously move through the same distance.

Figure 15:
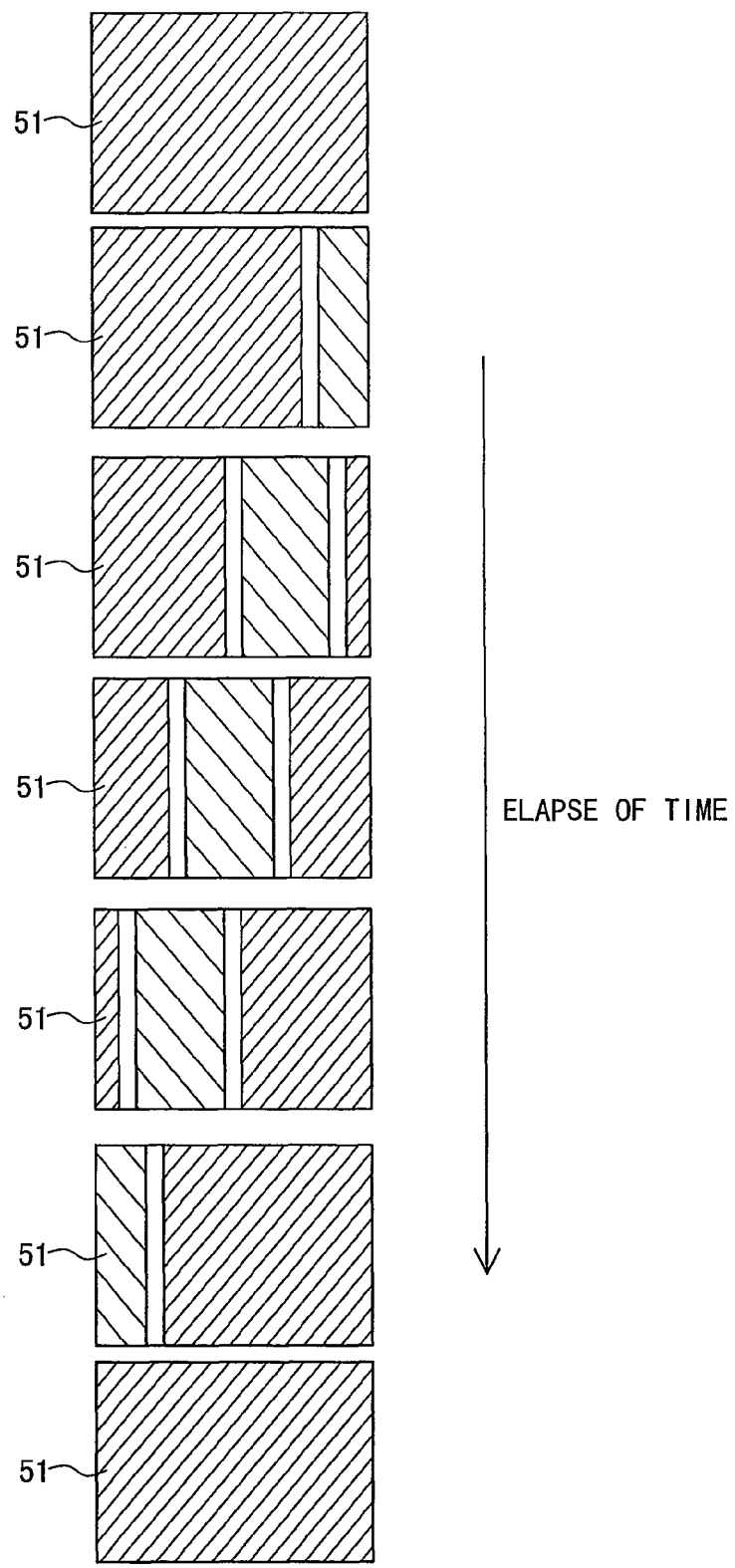
FIG. 15 is a diagram that describes an example of transmission data acquired according to the second embodiment of the present invention.

Multiple transmission images 51 that were acquired using this scanning method are shown in FIG. 15. In FIG. 14, the transmission images 51 are chronologically arranged in order from top to bottom, that is, in the order that the images were acquired during tomography in a scanning direction of the figure (from the left of the drawing to the right thereof). The two-dimensional tomograms 401 and three-dimensional stereoscopic images 401 constructed by image reconstruction arithmetic operations are substantially the same as in the first embodiment. The second embodiment uses the same image reconstruction algorithm as set forth in the description of the first embodiment. In addition, similarly to the first embodiment, if the radiation source 1 and the two-dimensional radiation detector 2 can be arranged facing each other across the pipe 10, the two devices can also be arranged to face, although not shown, in any direction other than vertically or horizontally with respect to the pipe 10.

Figure 16:
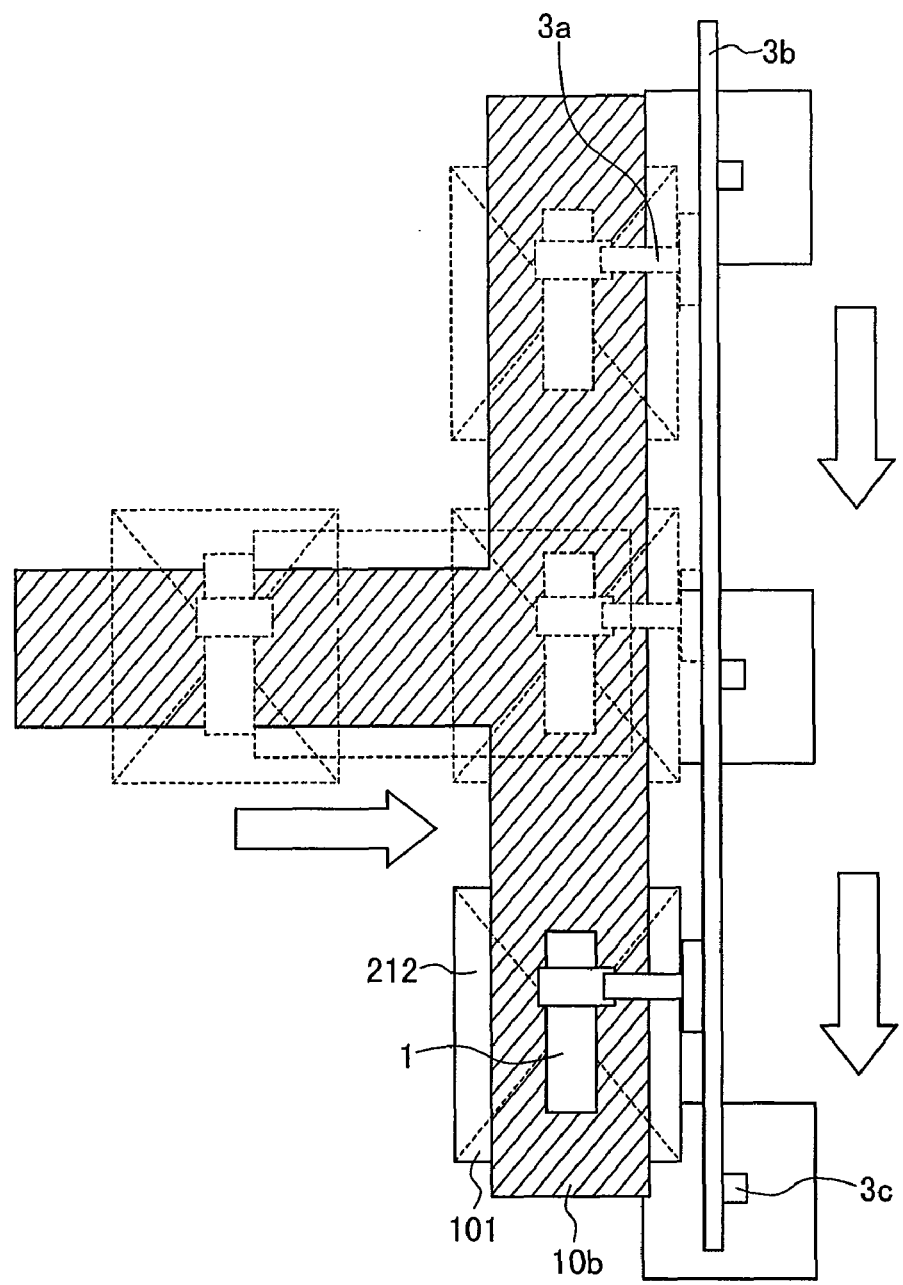
FIG. 16 is a diagram that describes an example of applying the second embodiment of the present invention.

FIG. 16 shows an example in which the apparatus of the second embodiment of the present invention is applied to tomographic imaging of a T-pipe 10b having a branching/meeting section. The T-pipe 10b when viewed from above of the apparatus is shown in this example. As shown, scanning in a major-axis direction of the T-pipe 10b is started from an upstream end of the branching/meeting section thereof. Scanning in the major-axis direction of the T-pipe is temporarily stopped after the apparatus has reached the branching/meeting section thereof. After that, an extend/retract unit of the supporting device 3 described in FIG. 15 is activated and the branching/meeting section of the T-pipe is scanned from a distal end thereof, through to a proximal end. The distal end and proximal end here refer to those of the pipe as viewed from the apparatus. After being scanned in this manner, the first section of the pipe is rescanned.

Third Embodiment

Figure 17:
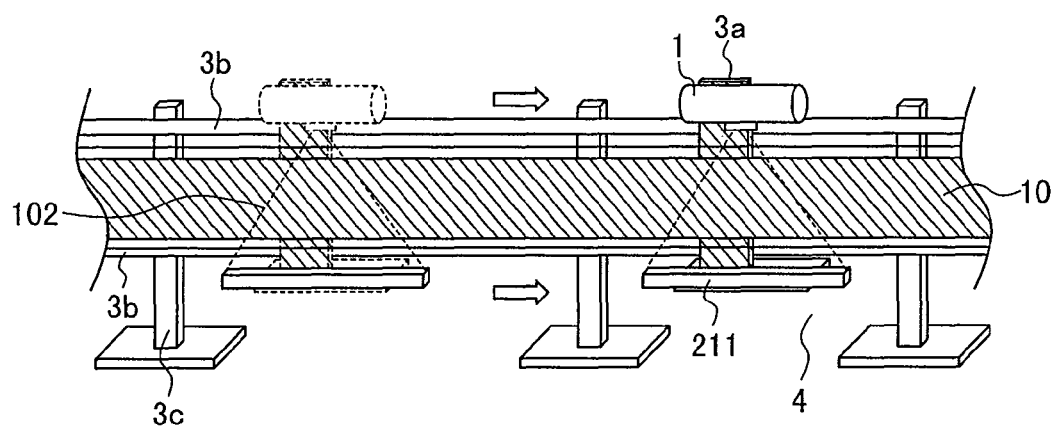
FIG. 17 is a diagram that describes a configuration of a third embodiment of the present invention.
Figure 18:
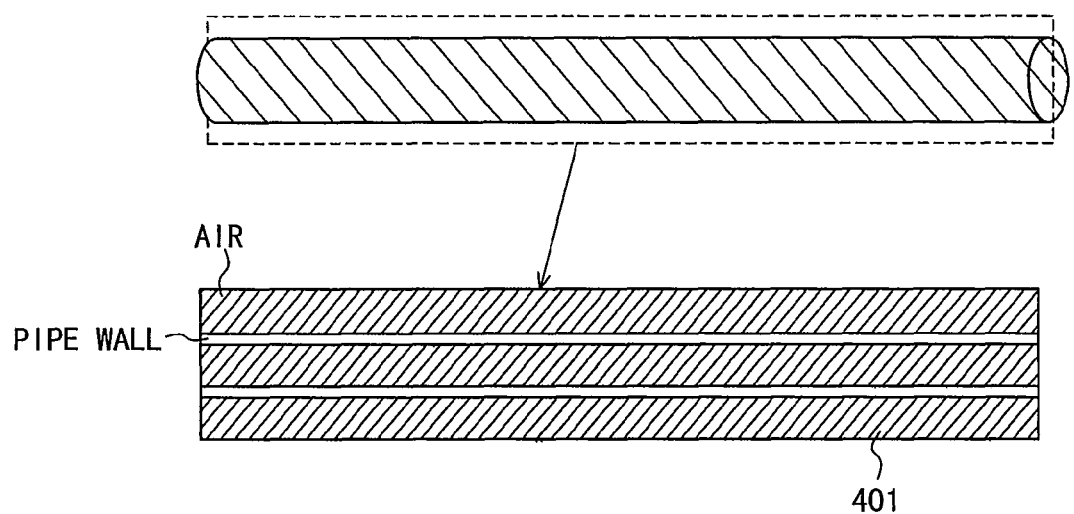
FIG. 18 is a diagram that describes an example of tomograms acquired according to the third embodiment of the present invention.

A third embodiment of the present invention is shown in FIG. 17. In the present embodiment, a one-dimensional radiation detector 211 called a line sensor functions as the radiation detector in the first embodiment. The one-dimensional radiation detector 211 has a shape of a slender bar and is disposed in an axial direction of a pipe. In this case, unlike tomography with the two-dimensional radiation detector 2, a fan-shaped beam of radiation (fan beam 102) is emitted from a radiation source 1. For this reason, a linear array of images are obtained as transmission images 51 during one detecting operation. As shown in FIG. 18, image reconstruction arithmetic results obtained using the plurality of transmission images acquired using this method become two-dimensional tomograms formed in a longitudinal cross-section of the pipe 10. An image reconstruction algorithm usable at this time can be the same as used in the first embodiment. In addition, similarly to the first embodiment or the second embodiment, if the radiation source 1 and the one-dimensional radiation detector 211 can be arranged to face each other across the pipe 10, the two devices can be arranged to face in any direction as well as vertically or horizontally with respect to the pipe 10.

Fourth Embodiment

Figure 19:
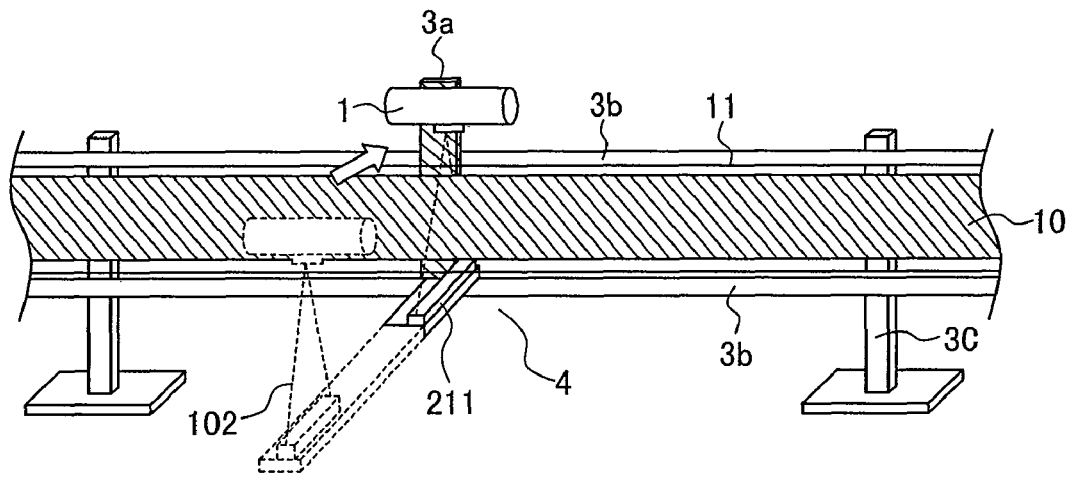
FIG. 19 is a diagram that describes a configuration of a fourth embodiment of the present invention.
Figure 20:
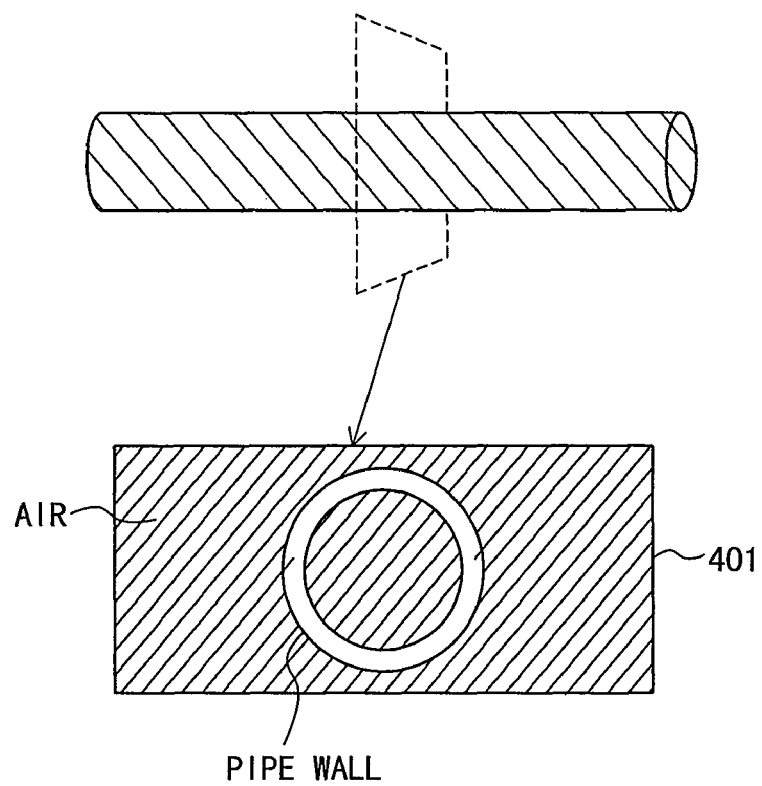
FIG. 20 is a diagram that describes an example of tomograms acquired according to the fourth embodiment of the present invention.

A fourth embodiment of the present invention is shown in FIG. 19. In the present embodiment, a one-dimensional radiation detector 211 called a line sensor functions as the radiation detector in the second embodiment. The one-dimensional radiation detector 211 is disposed vertically to an axial direction of a pipe. In this case, a linear array of images are obtained as transmission images 51 during one detecting operation. As shown in FIG. 20, image reconstruction arithmetic results obtained using the plurality of transmission images acquired using this method become two-dimensional tomograms formed in a longitudinal cross-section of the pipe 10 that is orthogonal to a major-axis direction thereof. An image reconstruction algorithm usable at this time can be the same as used in the first embodiment.

Figure 21:
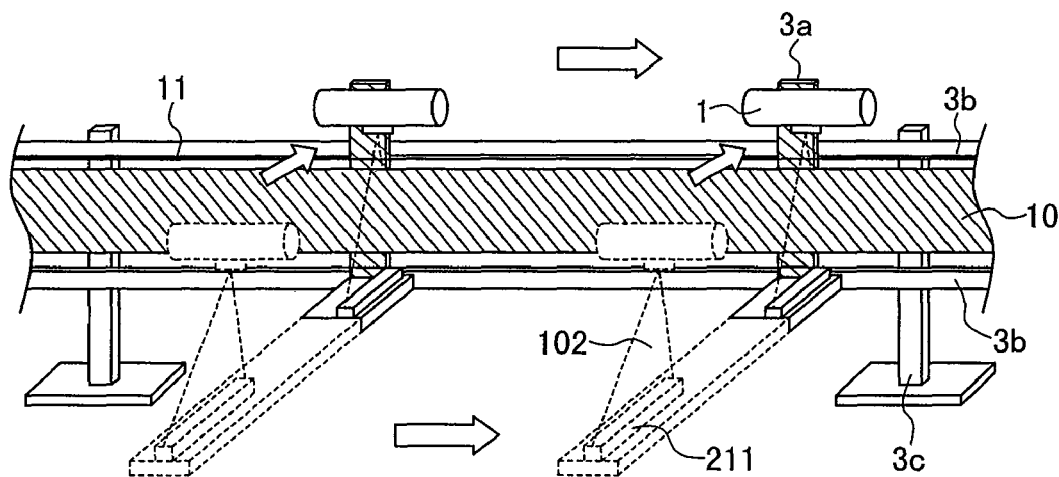
FIG. 21 is a diagram that describes an example of applying the fourth embodiment of the present invention.

FIG. 21 is a diagram explaining a method in which the scanning sequence shown in FIG. 19 is repeatedly applied to imaging in the major-axis direction of the pipe 10. This imaging method allows a three-dimensional stereoscopic image 402 of the pipe 10 to be constructed by overlaying tomograms at various positions shown in FIG. 20.

Fifth Embodiment

Figure 22:
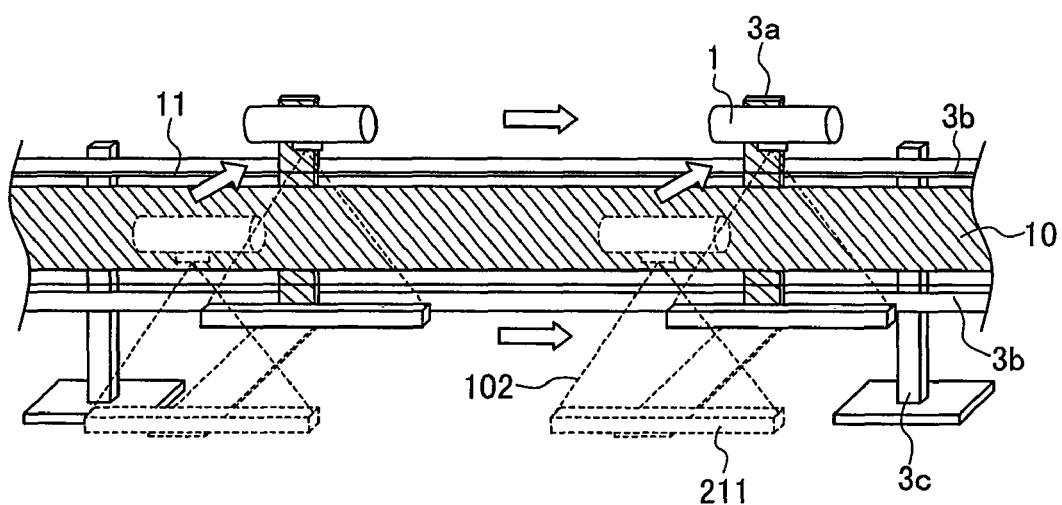
FIG. 22 is a diagram that describes a configuration of a fifth embodiment of the present invention.

A fifth embodiment of the present invention is shown in FIG. 22. The present embodiment applies to using a one-dimensional radiation detector 211 to form reconstructed images similar to those of the first embodiment. In the fifth embodiment, a radiation source 1 and the one-dimensional radiation detector 211 are first moved, as shown in FIG. 22, from a frontward direction of the drawing, in a rearward direction by an extendable unit of the supporting device 3a. Two-dimensional transmission images 51 at this position are acquired during one such scan. Next, a scanner 503 is moved through a distance "•u" and the above scan from the frontward direction of the drawing, in the rearward direction, is conducted once again. This sequence is subsequently repeated to scan in the major-axis direction of the pipe. A procedure for constructing two-dimensional tomograms 401 or a three-dimensional stereoscopic image 402 by conducting image reconstruction arithmetic operations based on the plurality of transmission images 51 obtained using this method is substantially the same as used in the first embodiment.

According to the above embodiments, tomography of the structures installed at specific locations can be performed speedily without searching for a scanning direction. Tomography of the structures installed in narrow and confined places is also possible. In addition, an apparatus that uses tomography to scan the structures installed at specific locations and even in narrow and confined places can be achieved in a simple apparatus configuration.

Sixth Embodiment

Figure 24:
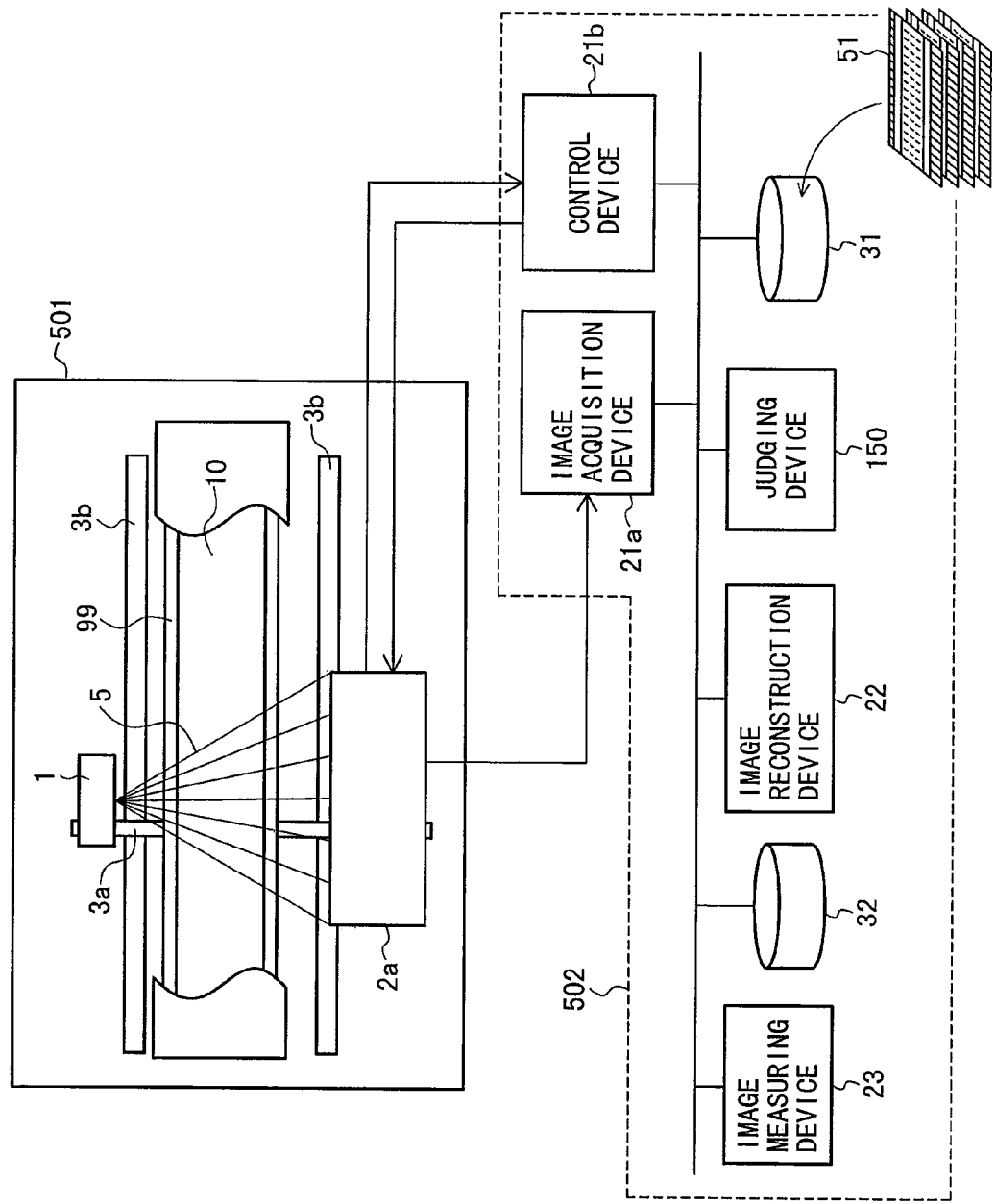
FIG. 24 is a system diagram that shows a radiation non-destructive inspection system (sixth embodiment)

FIG. 24 shows a system diagram based on one embodiment of the present invention. The system in FIG. 24, as with that of FIG. 1, includes an imaging system 501 and a control and arithmetic system 502. The control and arithmetic system 502 has: an image acquisition device 21a adapted so that signal levels equivalent to radiation intensity used during imaging of a pipe with a radiation detector 2a are acquired as a plurality of transmission images 51; a control device 21b that controls a scanner 503, a radiation source 1, and the radiation detector 2a; a transmission image storage device 31 into which the acquired plurality of transmission images 51 are stored as data; a judging device 100 that loads the plurality of transmission images 51 from the transmission image storage device 31 and then displays these images as stationary or dynamic images on a screen of a monitor such as a personal computer's so that the operator can enter an image reconstruction region as well as judgment results on whether image reconstruction is necessary; an image reconstruction arithmetic device 22 for reconstructing tomograms or three-dimensional stereoscopic images of the subject; and a reconstruction arithmetic result storage device 32 into which the reconstructed tomograms or three-dimensional stereoscopic images of the subject are stored.

When necessary, an image-measuring device 23 with image-measuring software or the like installed to implement image measurement based on the tomograms or on the reconstructed three-dimensional stereoscopic images can be added to provide convenience to the user.

Figure 23:
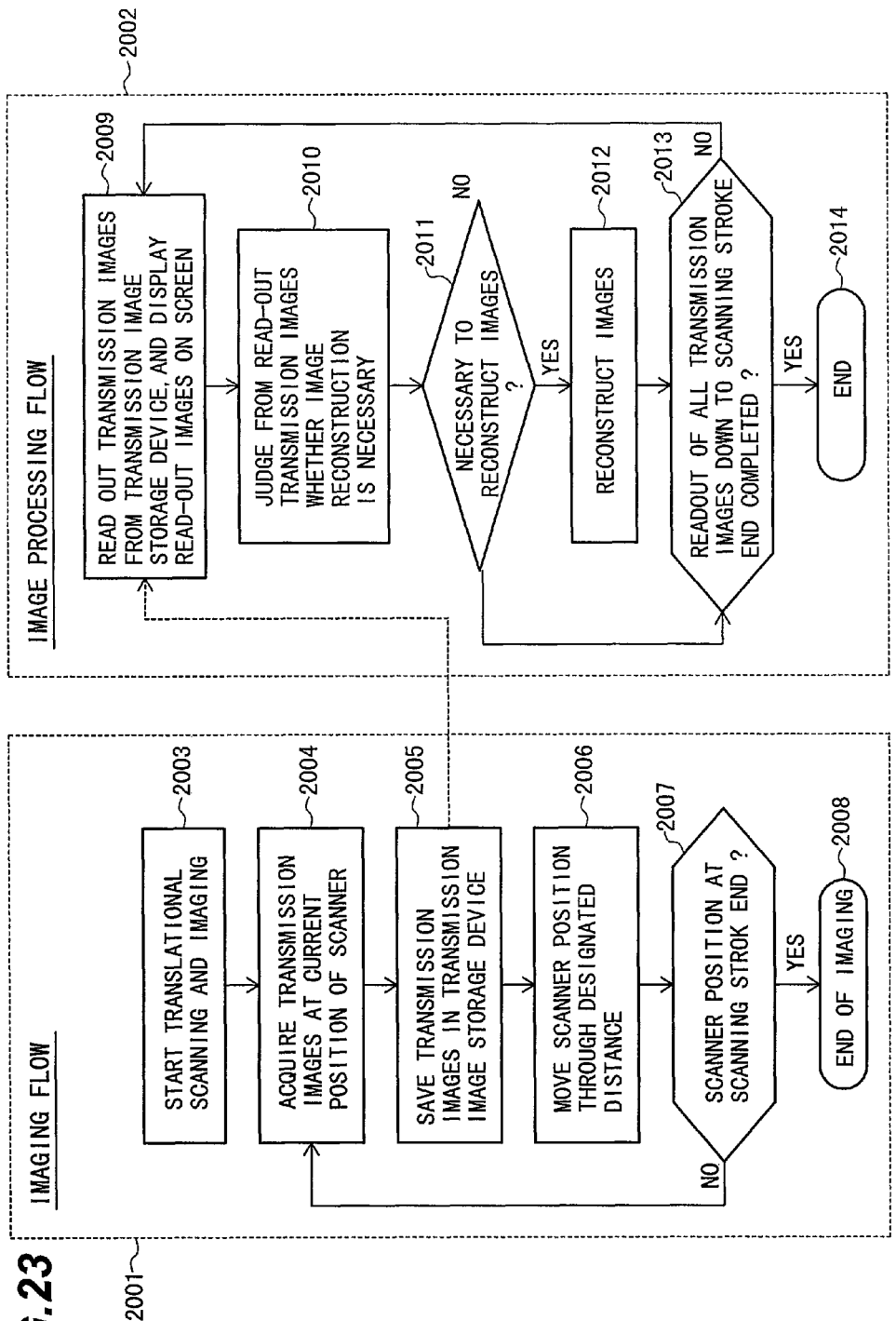
FIG. 23 is a total flow diagram of inspection method in the present invention.

FIG. 23 shows a flowchart of an inspection method used in the present invention. The inspection method in the present invention includes imaging flow 2001 for acquiring transmission image data by imaging, and image-processing flow 2002 for judging from acquired transmission image data whether image reconstruction is necessary, and executing image reconstruction.

In the imaging flow 2001, the scanner 503 moves the radiation source 1 and the radiation detector 2a in a longitudinal direction of the pipe and starts translational scanning (process 2003). The radiation source 1 emits radiation at a current position of the scanner, and after the radiation penetrating the pipe has entered the radiation detector 2a, transmission images are acquired (process 2004). The transmission image data that the image acquisition device 21a has acquired from the radiation detector 2a is saved in the transmission image storage device 31 (process 2005). Next, the control device 21b moves the scanner 503 through a designated distance in a major-axis direction of the pipe (process 2006) and judges whether the scanner 503 has reached an end of the pipe (process 2007). If the scanner 503 has not reached the end of the pipe in process 2007, process control is returned to process 2004 to acquire transmission images at the current scanner position. If the scanner 503 has reached the end of the pipe, imaging is finished (process 2008).

In the image-processing flow 2002, the saved transmission images in the transmission image storage device 31 are read out and when necessary, displayed on the screen of the judging device 100 (process 2009). Whether image reconstruction is necessary is judged from the transmission images that have been read out, and judgment results are entered into the judging device 100 (process 2010). A more specific example of the judging method will be described later herein. If defects or the like is detected on the subject of the inspection and image reconstruction is necessary (process 2011), the image reconstruction arithmetic device 22 is instructed to execute image reconstruction (process 2012). Details of the image reconstruction method will be described later herein. If the read-out transmission image data relates to the end of the pipe (the subject of the inspection), processing is finished, and if the image data does not relate to the pipe end, the readout process 2009 is repeated (process 2013). If, in the process 2011, the image reconstruction is judged to be unnecessary, whether the transmission image data relates to the end of the pipe is judged (process 2013).

According to this flowchart, image acquisition and image processing are concurrently executed, but image processing may occur after all necessary images have been acquired.

A more specific example of the imaging system 501 which is one constituent element of the present invention is described below. A way to create tomograms or three-dimensional stereoscopic images (reconstructed images) of the subject from the plurality of transmission images 51 that the imaging system 501 has acquired is also described below.

Figure 25:
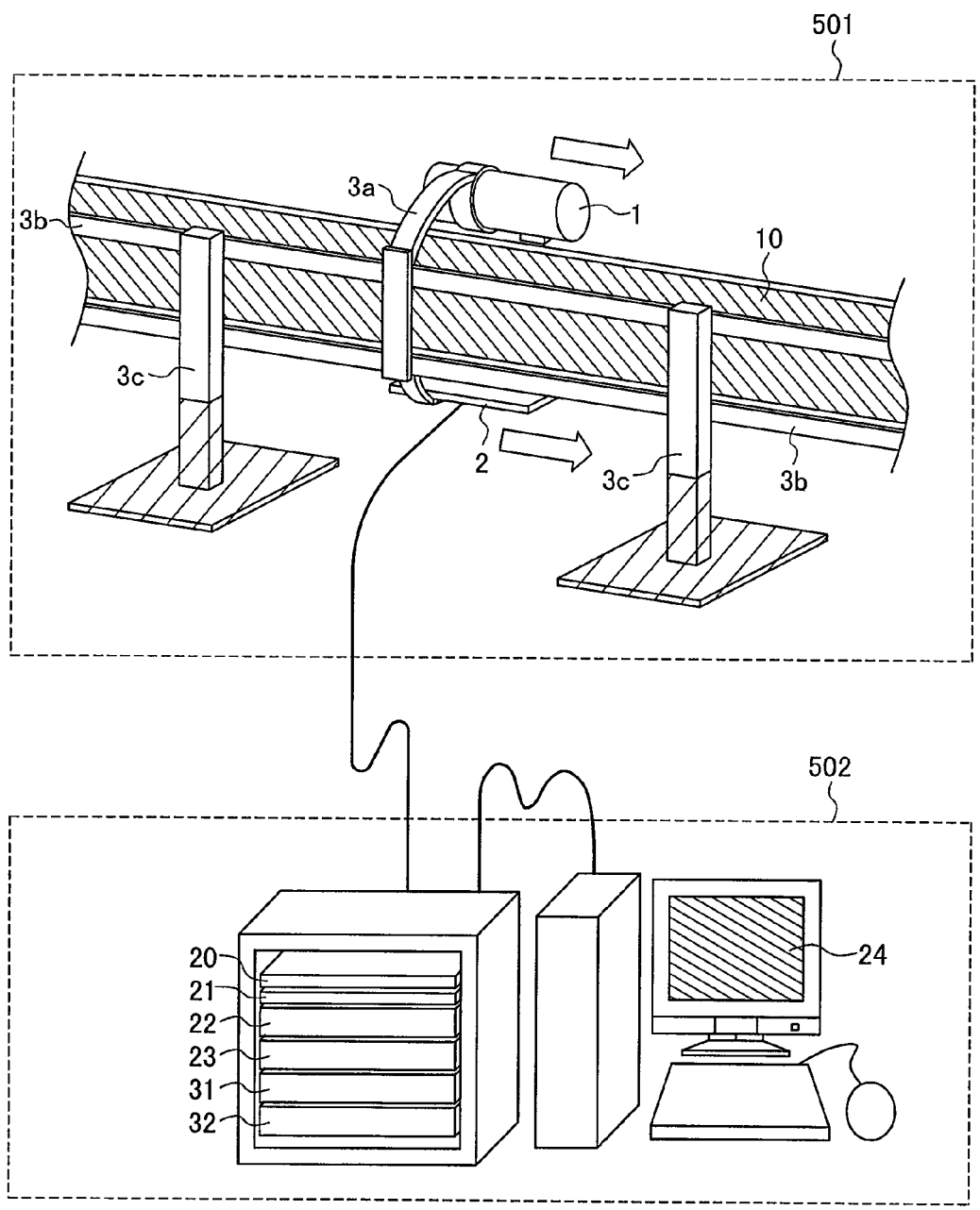
FIG. 25 shows a more specific example of the radiographic imaging apparatus used in the radiation non-destructive inspection system.

FIG. 25 shows a more specific example of the imaging system 501 and the control and arithmetic system 502. In this example, the radiation source 1 and the radiation detector 2a are supported by a supporting device (C-arm) 3a, and the supporting device (C-arm) 3a is moved along a guide rail 3b to execute scanning. The guide rail 3b is supported by support legs 3c set up on a floor, and disposed in the major-axis direction of the pipe 10 covered with a heat-insulating material. Also, the supporting device (C-arm) 3a is formed to be positioned along an outer surface of the pipe 10, across which the radiation source 1 and the radiation detector 2a are arranged to face each other.

As shown in FIG. 23, the transmission images of the pipe that are acquired for screening thereof can be used to reconstruct tomograms or three-dimensional images thereof, so data re-acquisition is unnecessary. This reduces inspection time, thus improving the inspection efficiency.

A basic process flow of the image reconstruction (process 2012 in FIG. 23) is substantially the same as the process flow shown in FIG. 9. In the present embodiment, however, a transmission image loading process 1002 and an air data loading process 1003 differ from those shown in FIG. 9. First transmission image data that has been acquired from those regions of the pipe which require image reconstruction for status confirmation of defective sections of the pipe, and second transmission image data that has been acquired before and/or after the acquisition of the first transmission image data are loaded during the transmission image loading process 1002 and air data loading process 1003 of the present embodiment. A logarithmic conversion process 1004 and subsequent processes are substantially the same as those of FIG. 9.

Use of the above-described imaging system 501 and limited-angle image reconstruction technique makes image reconstruction possible without acquiring new image reconstruction arithmetic data from the existing transmission image data.

The use of the above-described imaging system 501 and limited-angle image reconstruction technique also makes tomograms and stereoscopic images of the pipe acquirable. In this radiographic test (RT) method, therefore, any pipe sections that may have decreased in wall thickness can be positionally and quantitatively detected with high accuracy, compared with conventional RT. Additionally, even if the pipe to be inspected is as long as up to several meters, fast imaging of the pipe is possible. Furthermore, since imaging with a heat-insulating material mounted around the pipe can be conducted in a manner similar to that of RT, the step of removing or remounting the heat-insulating material is omittable during a start and end of the inspection, and thus the inspection efficiency can be improved.

Figure 26:
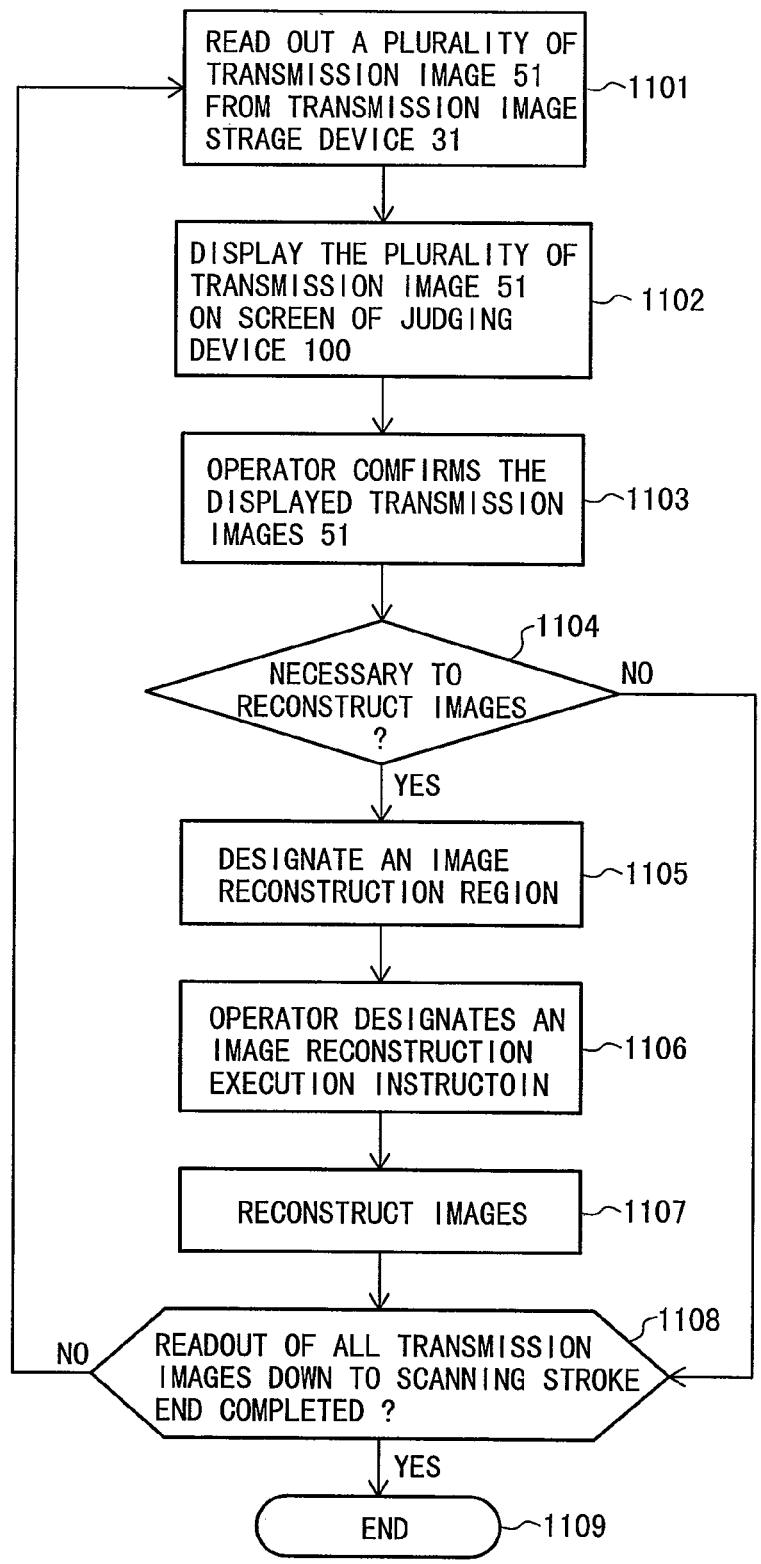
FIG. 26 is a flow diagram of inspection in the sixth embodiment.

Next, the image-processing flow 2002 in FIG. 23 is detailed using FIG. 26. In this inspection sequence, whether image reconstruction is necessary is judged in the judging device 100 for each section of the subject, and an area for reconstructing a three-dimensional stereoscopic image of the pipe is limited.

First, the judging device 100 reads out a plurality of transmission images 51 from the transmission image storage device 31 (process 1101). The plurality of transmission images 51 that have been read out are displayed on the screen of the judging device 100 (process 1102). The plurality of transmission images 51 are displayed in the form of stationary images or dynamic images on the screen. The operator visually confirms the displayed plurality of transmission images 51 and judges whether a three-dimensional image of the pipe is to be reconstructed for observing a solid shape thereof (processes 1103 to 1104). The judgment as to whether the image reconstruction is necessary may be based on judgment criteria of the operator or on criteria predetermined in accordance with documented standards. If a three-dimensional image (or a two-dimensional cross-sectional image) is to be reconstructed, the area for reconstructing the image is designated on the screen-displayed plurality of transmission images 51 via an input device of the judging device 100 (process 1105) and then an instruction for executing the image reconstruction is issued to the image reconstruction arithmetic device 22 (processes 1106 and 1107). These operations are repeated until the end of the pipe has been scanned (process 1108). If the image reconstruction is unnecessary, process control is transferred to process 1108 to continue processing.

Figure 27:
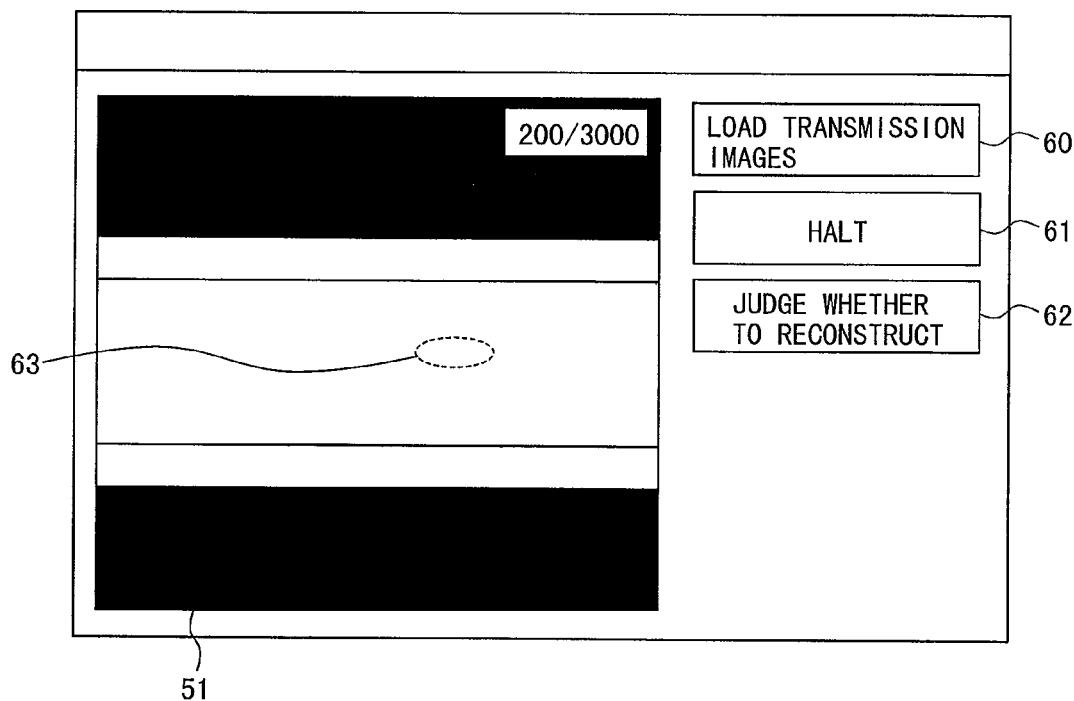
FIG. 27 is a diagram that describes an example of transmission image display.
Figure 28:
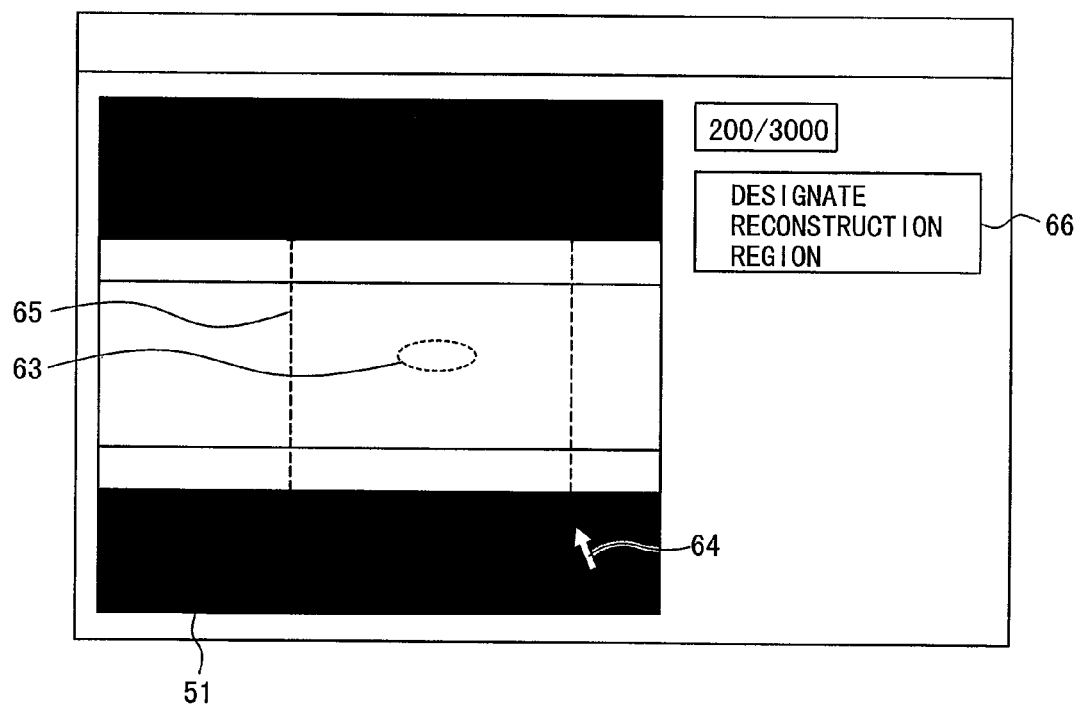
FIG. 28 is a diagram in which a reconstruction area is designated in a transmission image.

Examples of a screen display made when a plurality of transmission images 51 are displayed on the screen of the judging device 100 are shown in FIGS. 27 and 28. In these figures, a press of a transmission image loading button 60 loads the transmission images from the transmission image storage device 31 and displays the plurality of transmission images 51 as dynamic images on the screen. These transmission images 51 appear as if images of the subjects 10f and 10g positioned between the radiation source 1 and the radiation detector 2a were superimposed depth-wise as shown in FIG. 7. A thinned-down section 63 of the pipe can therefore be displayed in a contrast display format on each transmission image 51 without reconstructing a three-dimensional image or two-dimensional image of the pipe. In addition, the thinned-down section 63 or other defective sections of the pipe can be screened by using these transmission images to dimensionally reduce the two-dimensional or three-dimensional image reconstruction area, and thus to reduce the amount of data operated on for the image reconstruction. Furthermore, since there is no need to conduct the reconstruction over the entire length of the pipe, the reconstructed-image storage device for saving the three-dimensional or two-dimensional image can be reduced in storage capacity. Accordingly, inspection efficiency for the pipe can be improved.

After confirming each transmission image 51 and finding the thinned-down section 63 of the pipe, the operator presses a button 61 that stops the display of the dynamic images in order to confirm the thinned-down section 63 on the three-dimensional image of the pipe. Next, the operator enters judgment results by pressing a button 62 for judging whether the image reconstruction is necessary.

If the image reconstruction is judged to be necessary, the screen display changes to that of FIG. 28. On this new screen display, a reconstruction area 65 is designated using a pointer 64 of the PC-connected input device such as a mouse, and a button 66 is pressed to execute arithmetic operations. The press of the button 66 sends an image reconstruction command to the image reconstruction arithmetic device 22. The reconstruction area 65 can be designated by surrounding the thinned-down section 63 of the pipe with a rectangle.

Figure 29:
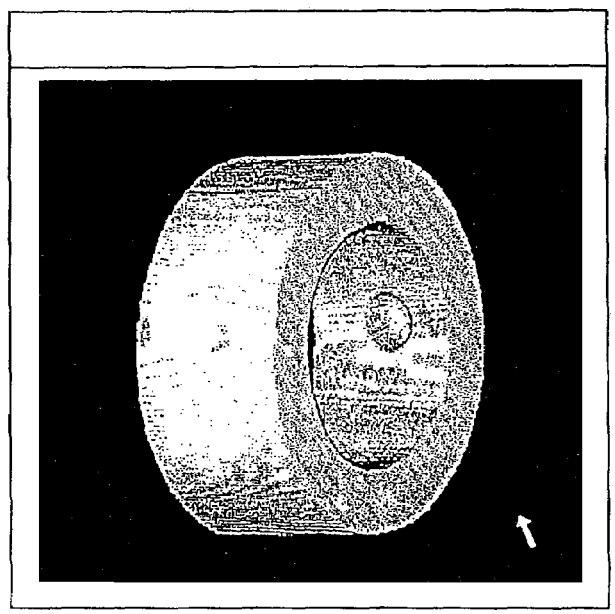
FIG. 29 is a diagram that describes an example of image reconstruction arithmetic results display.

FIG. 29 shows a two-dimensional tomogram or three-dimensional stereoscopic image on-screen representation of the pipe section equivalent to the reconstruction area 65 on the transmission image. The reconstruction of this two-dimensional tomogram or three-dimensional stereoscopic image allows the operator to easily confirm the solid shape of the thinned-down section 63 of the pipe. If it is suspected that the transmission image data indicates a pipe defect such as a reduction in wall thickness, confirming only the particular defective section of the pipe on the two-dimensional tomogram or three-dimensional stereoscopic image thereof during the above operational sequence makes it possible to reduce the inspection time significantly and improve inspection efficiency, without reconstructing a two-dimensional tomogram or three-dimensional stereoscopic image that spans the entire length of the pipe. In addition, if the generation of the reconstructed image involving a large data volume is limited to a part of the pipe, the storage capacity of the reconstructed-image storage device can be reduced.

Figure 30:
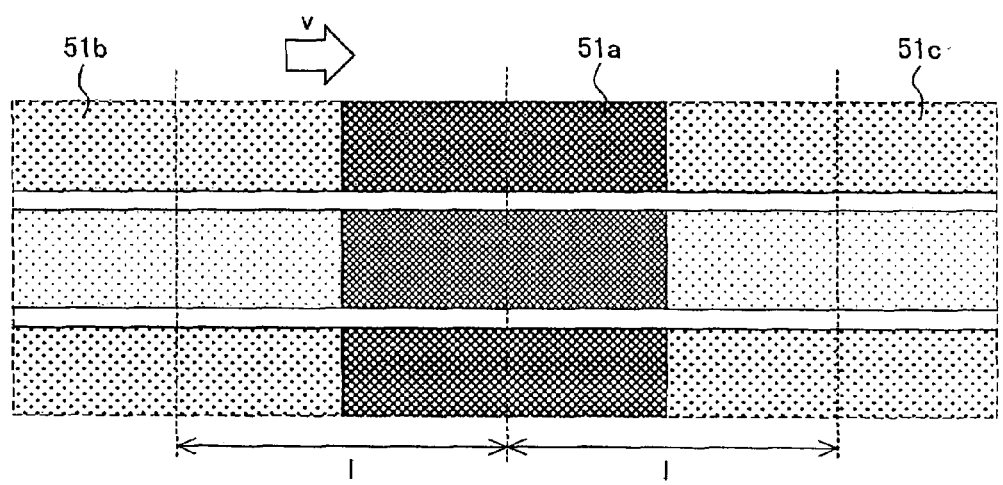
FIG. 30 is a diagram that describes an example of a method for determining automatically a transmission image range used in an image reconstruction arithmetic process.

In addition to area designation with the input device described above, automatic designation based on arithmetic parameters is available to designate the reconstruction area (see FIG. 30 for the latter method). An example of a transmission image data range usable for the image reconstruction is shown in FIG. 30. FIG. 30 indicates that when a first transmission image 51a that has been judged to require image reconstruction is taken as a reference image, the range of the transmission images to be used for the image reconstruction can be determined by length "l" (mm) of the transmission image 51a in an associated scanning direction, a moving velocity "v" (mm/sec) of the radiation source 1 and radiation detector 2a, and a scanning rate (frame image acquisition rate) "f" (frames/sec) of the radiation detector 2a. That is to say, when the middle image shown in FIG. 30 is the first transmission image 51a mentioned above, a data size of its anterior and posterior images (51b and 51c) to be used as second transmission image data is calculated using expression (2).

Data size of the transmission image data to be used
for image reconstruction=$f(2\times l)/v+1$ (frames)  (Expression 2)

If the image reconstruction is judged to be unnecessary, the screen display state does not change to that of FIG. 28 and the display of dynamic images is restarted.

It is conceivable that pipe inspection at sites such as an electric power plant is intended to examine a thickness reduction status of the pipe wall and to seek for foreign matter entrained in the pipe interior. In these cases, since all information in the scanning direction is displayed in superimposed form, an initial phase of the reduction in wall thickness and the presence of small foreign matter are usually difficult to discriminate on the transmission image data. It is desirable, therefore, that after the confirmation of the plural transmission images displayed on the screen, the apparatus should be operated such that if it is suspected that there is a defective section, image reconstruction is judged to be necessary and tomograms or a stereoscopic image is reconstructed for closer inspection.

Seventh Embodiment

Figure 31:
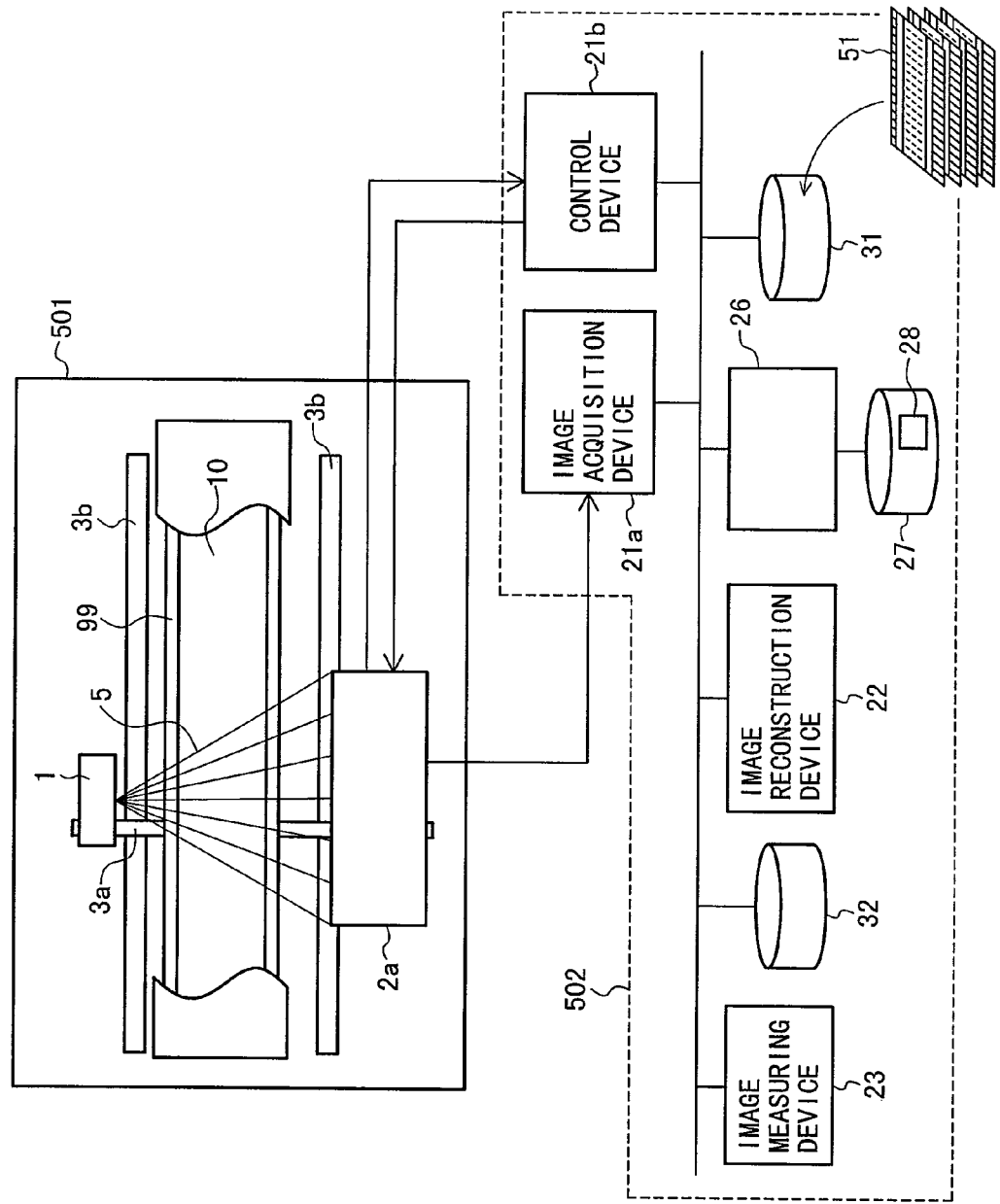
FIG. 31 is a system diagram that shows a radiation non-destructive inspection system (seventh embodiment)

A system diagram based on another embodiment of the present invention is shown in FIG. 31. The system shown in this figure includes an input device 26 for entering the kind of material of the subject or a linear attenuation coefficient "•" thereof or a size thereof. The input device 26 is used instead of the judging device 100 in FIG. 24, and functions as a reference data input device for entering reference data for an aid in judging whether image reconstruction is necessary. The system also includes a storage device 27 that contains an attenuation calculation program 28.

Figure 32:
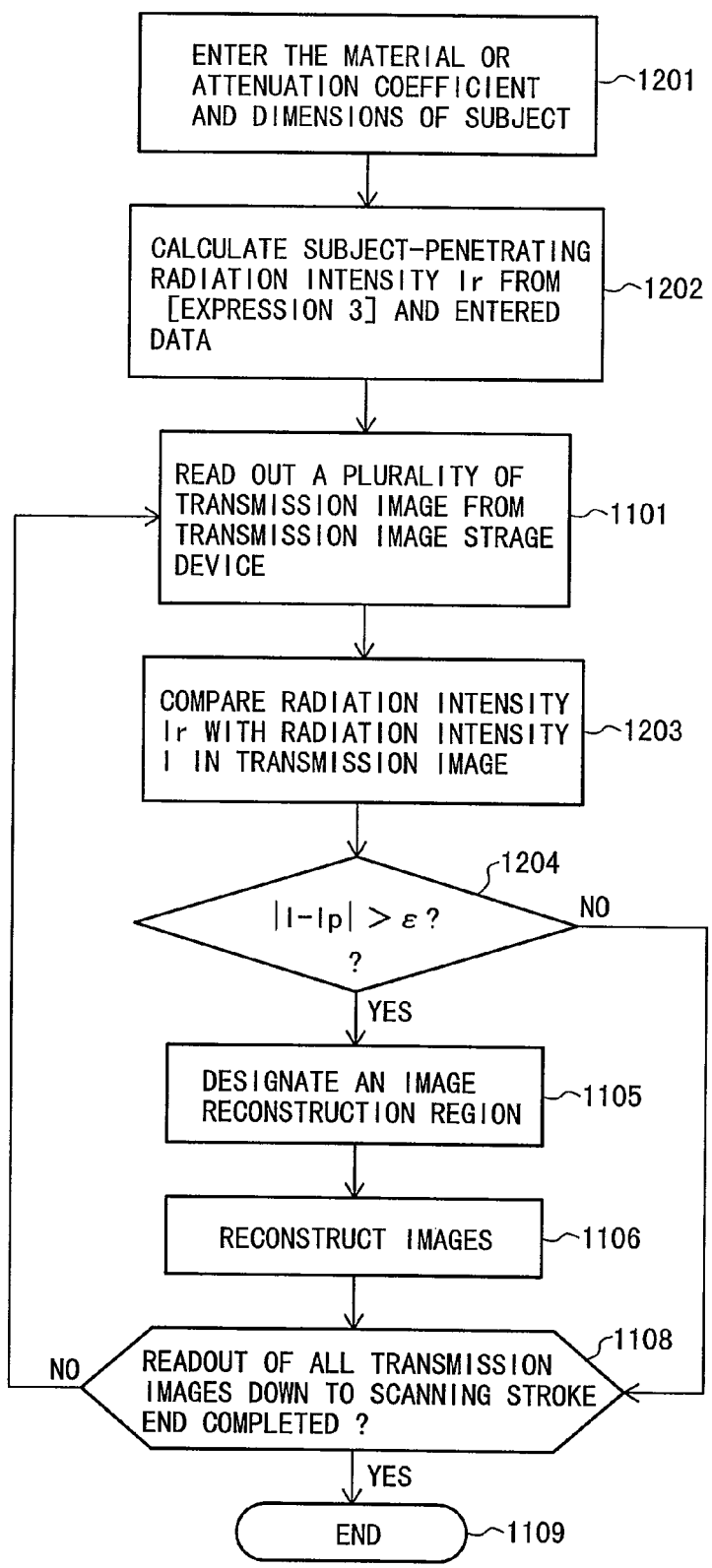
FIG. 32 is a flow diagram of inspection in the seventh embodiment.

A process flow of the present embodiment is shown in FIG. 32. In this process flow, processes 1201 and 1202 are additionally inserted in front of the process 1101 in the image-processing flow sequence (FIG. 26) of the sixth embodiment. Also, the processes 1102 and 1103 in FIG. 26 are replaced by a process 1203, and a judging parameter is assigned in a process 1204.

The process 1201 is provided for the operator to enter the kind of material or linear attenuation coefficient "•" and size of the subject from the input device 26. The process 1202 activates the attenuation calculation program 28 to calculate radiation intensity "$I_r$" from the data that was entered in the process 1201 and expression (3). The intensity "$I_r$" is an energy level of the radiation which penetrated the subject.

$$I_r = I_o \exp(-\mu t) \quad \text{(Expression 3)}$$

where "$I_s$" denotes unattenuated radiation intensity and "t" denotes penetration length of the radiation through the subject. The size of the subject that was entered in the process 1201 is used as "t". In addition, if the kind of material of the subject is entered in the process 1201, a database of an attenuation coefficient associated with the same kind of material pre-registered in the storage device 27 is referred to and this attenuation coefficient is converted into a "•" value.

The process 1203 serves as a data comparator to compare radiation intensity "$I_r$" that was calculated by the attenuation calculation program 28, and radiation intensity "I" of each transmission image saved in the transmission image storage device. That is to say, the process 1203 compares the "$I_r$" level calculated in the process 1202, and the radiation intensity "I" in individual pixels of the transmission image. For comparison with "I" in each pixel of the transmission image, the calculation of "$I_r$" using expression (3) needs to be conducted for each pixel position of the transmission image with the specific geometry of the device taken into account.

It is to be understood that under the judging parameters in the process 1204, the data comparator uses a threshold level experimentally preassigned by the operator, and that if this level is exceeded, the image reconstruction is conducted.

The process 1105 can use the method set forth in the sixth embodiment.

As can be seen from the above, the use of the judging parameters based on the process 1204 allows accurate judgment, even if the pipe has defective sections difficult to visually find.

According to the present embodiment, simplified and rapid processing is possible for cubic or cylindrical bodies and other subjects of a simple shape, since the penetration length "t" can be geometrically calculated.

Since attenuation levels are calculable from radiation intensity, judgments can also be based on comparisons between the attenuation levels. The same also applies in the embodiments described below.

Eighth Embodiment

Figure 33:
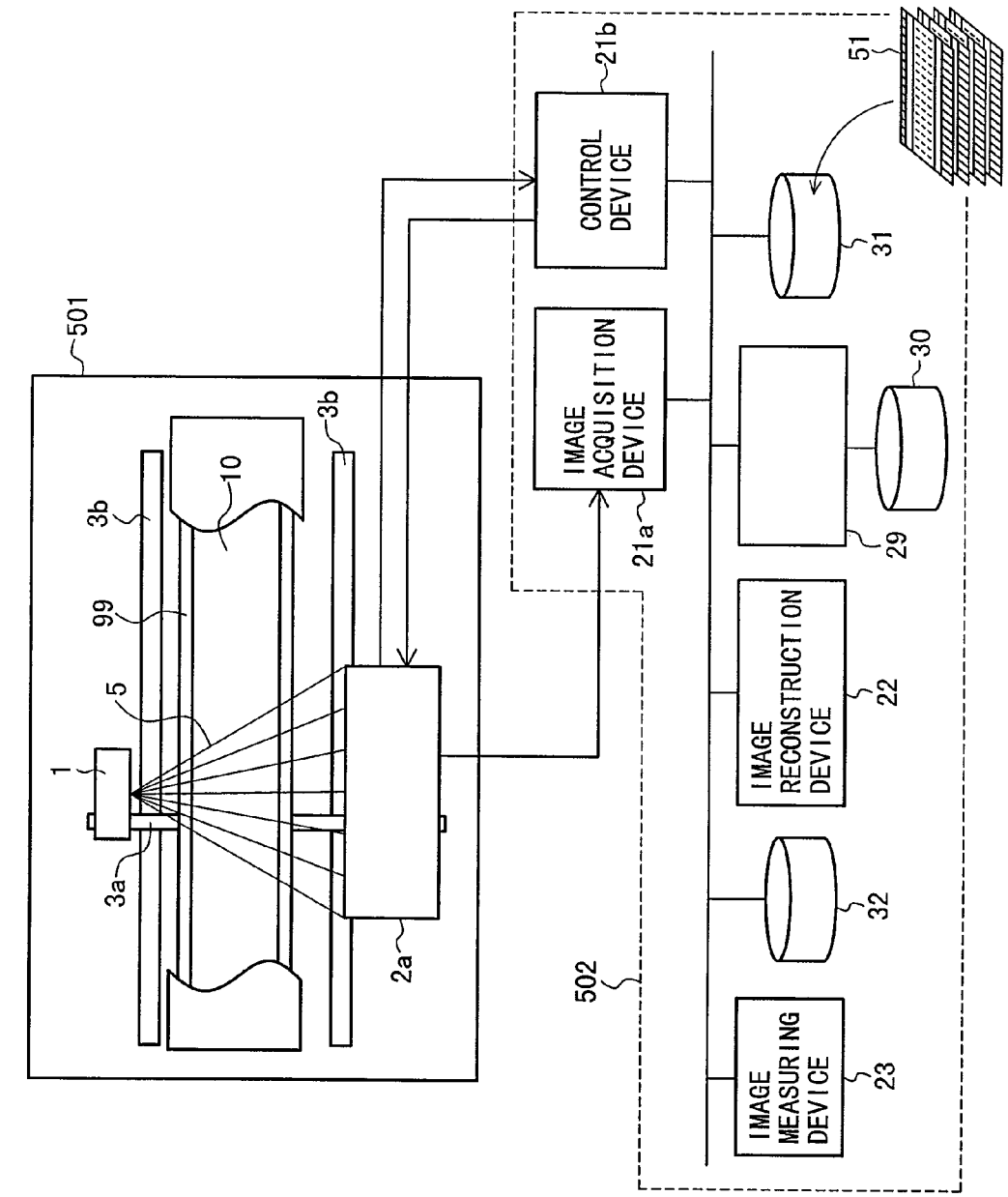
FIG. 33 is a system diagram that shows another radiation non-destructive inspection system (eighth embodiment)

A system diagram based on yet another embodiment of the present invention is shown in FIG. 33. The system shown in this figure includes an arithmetic device 29 that uses CAD data of the subject to execute simulation, and a storage device 30 that contains the CAD data of the subject and a simulation program. The arithmetic device 29 and the storage device 30 replace the input device 26 and storage device 27 shown in FIG. 31.

Figure 34:
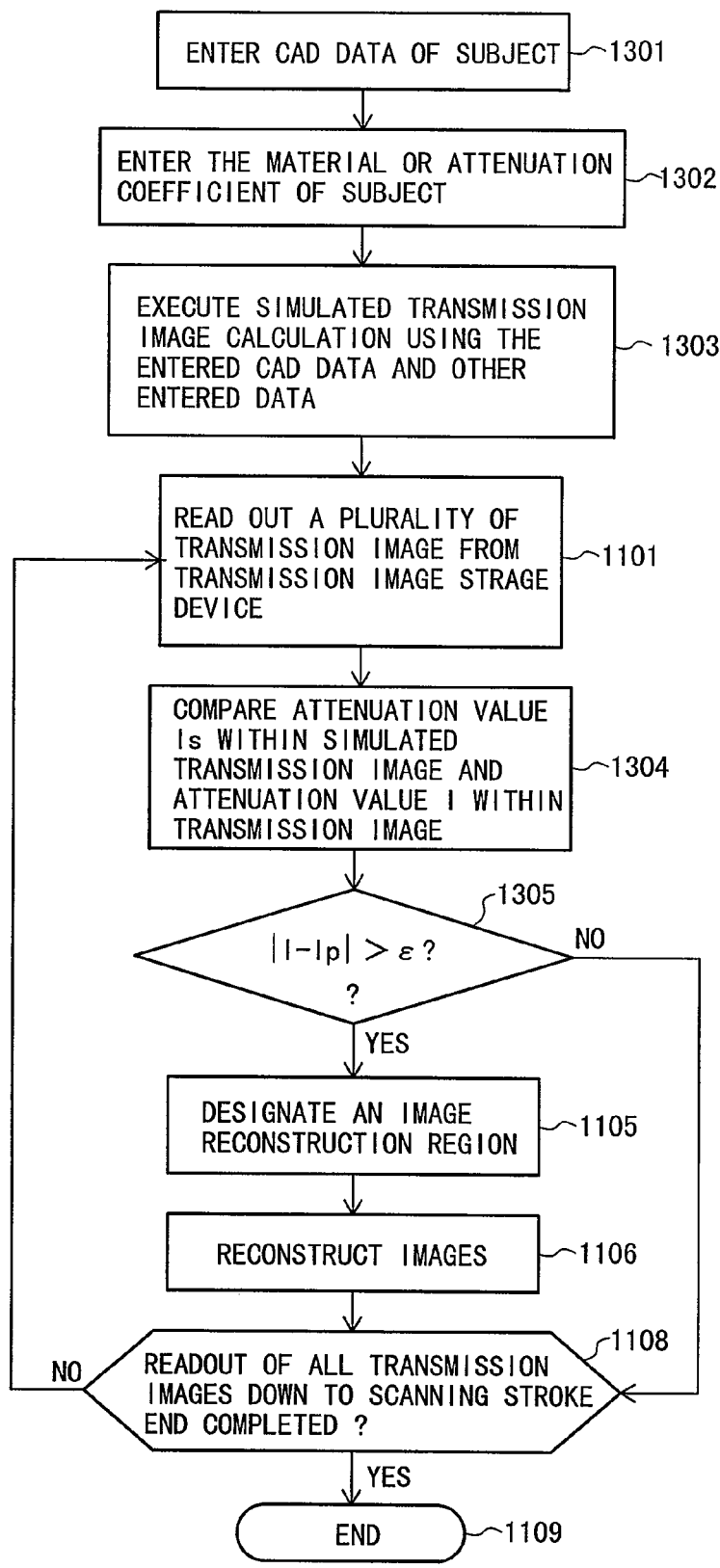
FIG. 34 is a flow diagram of inspection in the eighth embodiment.

A process flow of the present embodiment is shown in FIG. 34. In this process flow, processes 1301 to 1303 replace the processes 1201 and 1202 conducted in the image-processing flow sequence of the seventh embodiment. Also, processes 1304 and 1305 replace the processes 1203 and 1204, respectively.

The process 1301 is used to enter the CAD data of the subject into the storage device 30. The process 1302 is used to enter the kind of material of the subject or the attenuation coefficient thereof into the storage device 30. The process 1303 is conducted for the arithmetic device 29 to simulate the penetration of radiation by arithmetic operations with the entered data and other data. The arithmetic device 29 calculates the transmission images in the CAD data.

Figure 35:
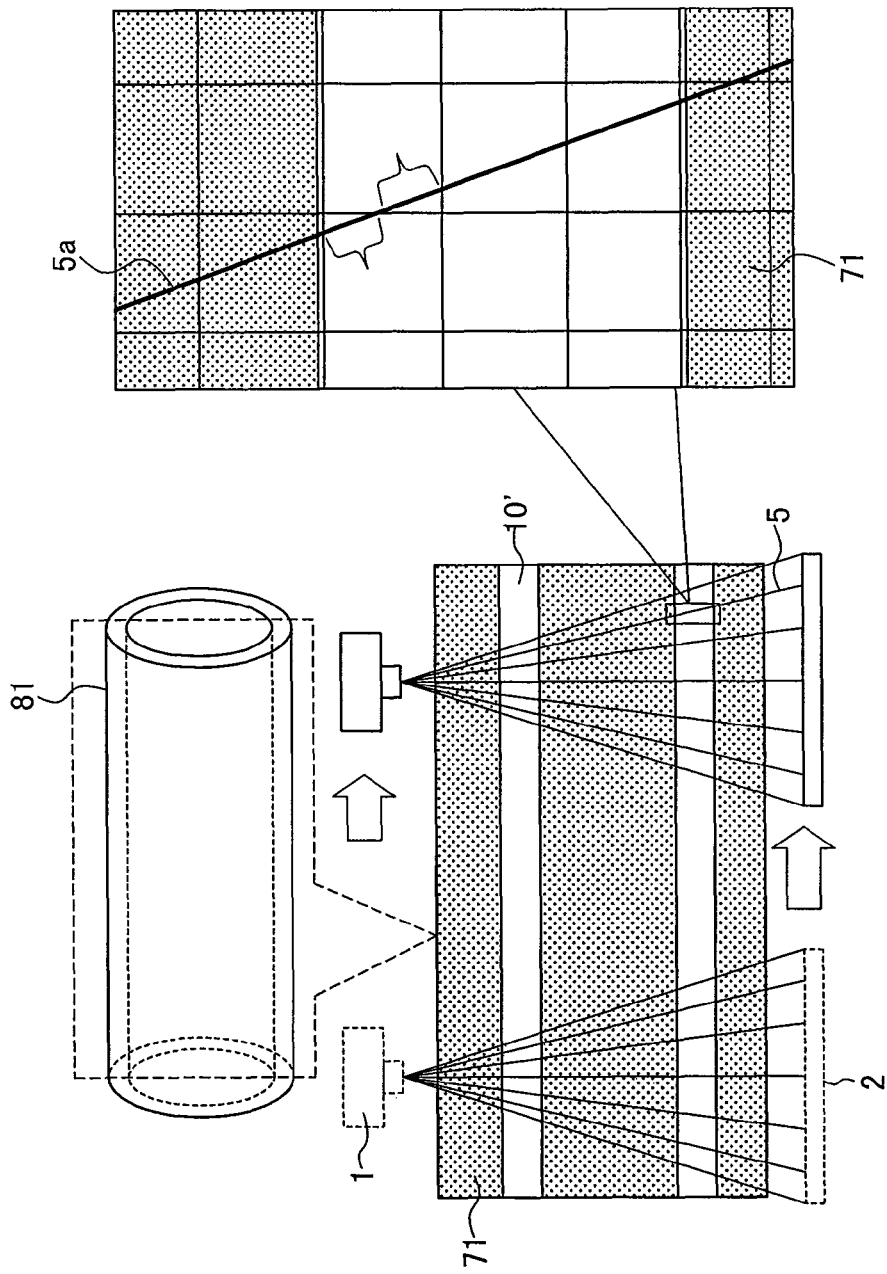
FIG. 35 is a diagram that describes simulation based on CAD data.

FIG. 35 shows a schematic diagram of the simulation in the process 1303 by the arithmetic device 29 using the CAD data. Two-dimensional simulation relating to a cross section represented by a dotted line in the CAD data 81 is shown for simplicity in the figure. The cross-sectional image in the CAD data 81 is generated as a two-dimensional, bit-mapped image 71 by rasterizing or the like. As shown in the enlarged diagram located to the right of the figure, the bit-mapped image is separated by very small square grids. The radiation penetration path 5a connecting a radiation emission point of the radiation source 1 and each element of the radiation detector 2a crosses each grid of the bit-mapped image 71. Length of this radiation penetration path 5a, and the value of "•" that is associated with a pixel value in the each grid are multiplied. The thus-obtained product for each grid is added over all grids that the radiation penetration path 5a crosses. The radiation intensity "$I_s$" in each radiation detector element, based on the simulation, is calculated using expression (4).

$$I_s = I_o \exp\left(-\sum_i \mu_i t_i\right) \quad \text{(Expression 4)}$$

where "$I_s$" denotes unattenuated radiation intensity. Also, "$\mu_i$" denotes the linear attenuation coefficient in the ith grid which the radiation penetration path 5a crosses, and "$t_i$" denotes penetration length of the radiation through the grid.

In the process 1101, transmission images that the radiation detector 2a obtained during the imaging of the pipe are read out from the transmission image storage device 31.

In the processes 1304 and 1305, an attenuation ratio of each transmission image obtained above, and that of each transmission image obtained by the CAD data simulation are compared and a judgment on whether image reconstruction is necessary follows. Subsequent processing steps are substantially the same as in the second embodiment.

According to the present embodiment, since a bit-mapped image based on CAD data can be used as an input, processing is possible, even for pipe-mounted valves, socket pipe connectors, and other fittings whose simple geometric calculation is difficult because of a complex shape. In addition, processing is possible, even when the products of the same kind or of the same lot, discussed in the following embodiments, cannot be used.

Ninth Embodiment

Figure 36:
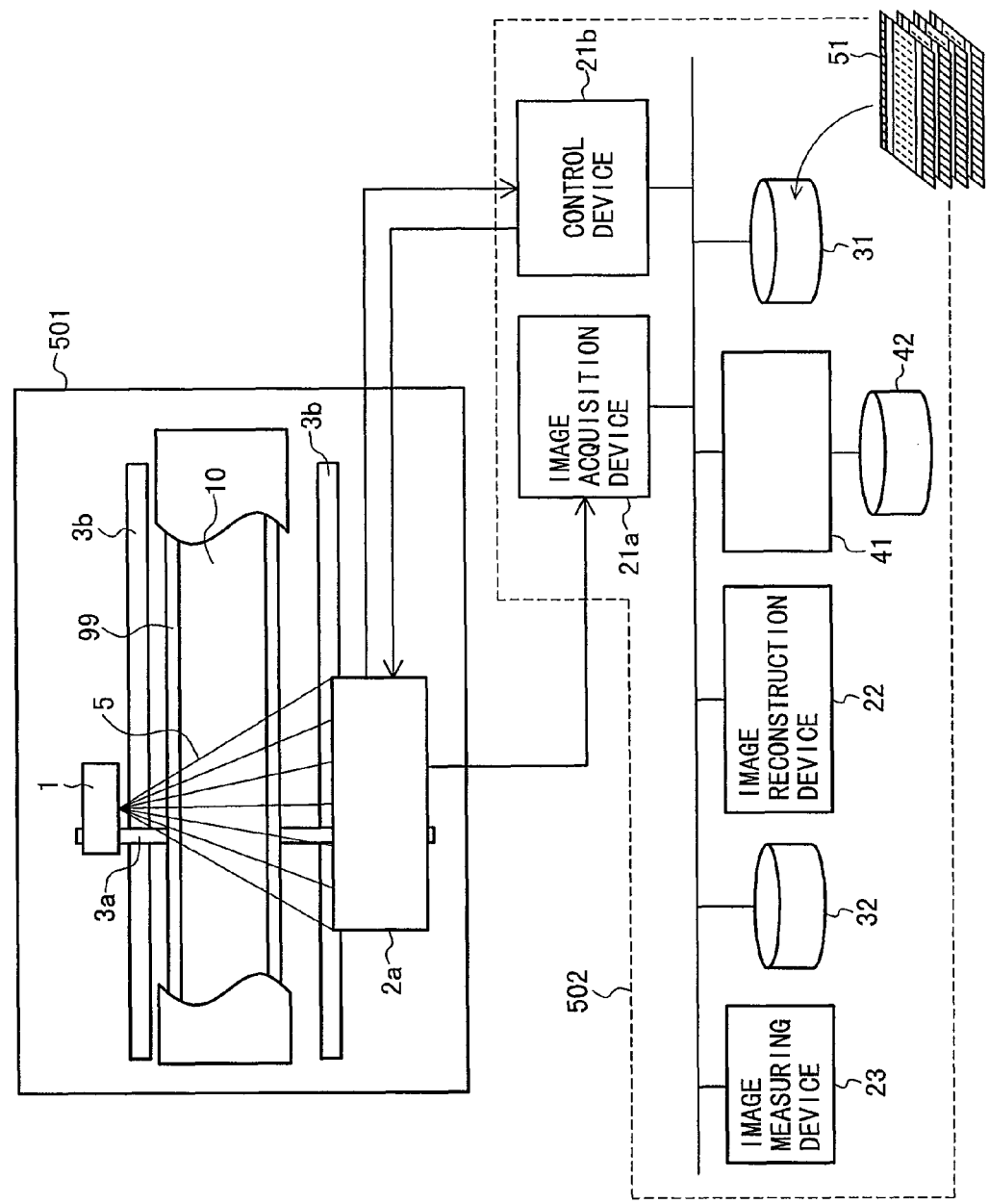
FIG. 36 is a system diagram that shows yet another radiation non-destructive inspection system (ninth embodiment)

A system diagram based on a ninth embodiment of the present invention is shown in FIG. 36. The system shown in this figure includes an arithmetic device 41 that conducts comparative arithmetic operations on attenuation levels between transmission images, and a storage device 42 into which a previously acquired plurality of transmission images are stored. The arithmetic device 41 and the storage device 42 replace the arithmetic device 29 and storage device 30 shown in FIG. 33.

Figure 37:
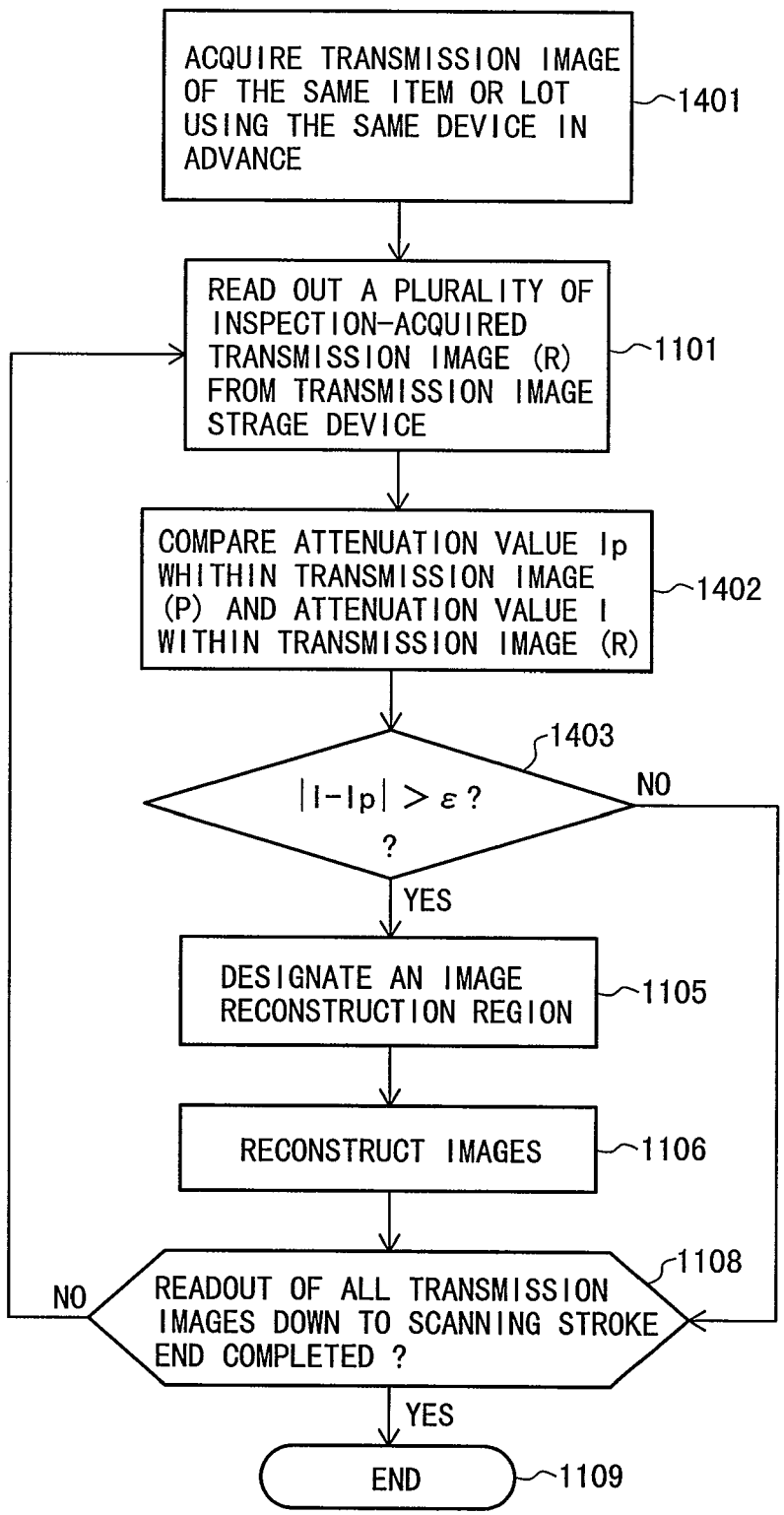
FIG. 37 is a flow diagram of inspection in the ninth embodiment.

A process flow of the present embodiment is shown in FIG. 37. In this process flow, a process 1401 replaces the processes 1301 to 1303 conducted in the inspection flow sequence of FIG. 34. In the process 1401, the plurality of transmission images (P) 51 that the imaging system 501 has acquired in advance during imaging of a product of the same kind or of the same lot are stored into the storage device 42 prior to inspection with the system. Processes 1402 and 1403 are based on the same concept as that of the processes 1304 and 1305, respectively, in FIG. 34, and only differ from these processes in the kind or nature of data used for comparisons.

In the process 1101, transmission images (R) that were acquired during the inspection are loaded from the transmission image storage device 31 by the arithmetic device 41.

In the processes 1402 and 1403, the attenuation level in the transmission image (P) that was acquired in advance during imaging for the product of the same kind or of the same lot, and the attenuation level in one transmission image (R) which was acquired during the inspection are compared in the arithmetic device 41. Image reconstruction occurs if comparison results indicate a data difference exceeding a predetermined threshold level. This judging method allows judging to be performed based on an actual product. In addition, changes in characteristics of the subject with time can be examined and analyzed by scanning products of the same kind.

According to the above embodiments, since the transmission image data used for screening to search for a defective section of the pipe is the same as the data required for the reconstruction of tomograms or three-dimensional stereoscopic images, data re-acquisition is unnecessary and the inspection time can be reduced for higher inspection efficiency.

In addition, since an area that applies image reconstruction can be easily selected by screening based on transmission images, there is no need to reconstruct images over the entire length of the pipe. The amount of data to be operated on for image reconstruction can therefore be reduced and the inspection efficiency improved.

Furthermore, since screening based on transmission images allows easy selection of an area that applies image reconstruction, the amount of data required for the generation of tomograms or three-dimensional stereoscopic images can be reduced and the inspection efficiency improved.

The embodiments of the present invention offer the following advantageous effects: for products of the same kind, since images other than those of defective sections of the pipe contain no shape errors, changes in the characteristics only of the defective sections can be examined and analyzed very accurately; for products of the same lot, since shape errors between the products are insignificant, defective sections can be identified very accurately, even when products of the same lot cannot be used; and even when CAD data is absent, processing is possible.

Using the system of the present invention makes radiation-based inspection efficient and executable for large structures such as the wings of aircrafts, as well as for the pipes set up at electric power plants.

What is claimed is:

1. An X-ray radiation non-destructive inspection system, comprising:
an X-ray radiation source and a two-dimensional X-ray radiation detector for moving on a guide rail which is arranged along a longer direction of a pipe which is installed in a plant which is a subject of inspection, and arranged oppositely to each other across the pipe;
a C-shaped arm fixing said X-ray radiation source and said two-dimensional X-ray radiation detector for scanning said X-ray radiation source and said two-dimensional X-ray radiation detector along the pipe side by side; and
a control and arithmetic apparatus for acquiring transmission image data from said two-dimensional X-ray radiation detector for every fixed distance which moves on said C-shaped arm, in which the transmission image data include data at a projection part of a first subject of inspection and a projection part of a second subject of inspection which is located at a different depth from the first subject of inspection;
wherein said control and arithmetic apparatus comprises:
an image acquisition device for acquiring the transmission image data output from said two-dimensional X-ray radiation detector;
a control device for controlling a position of said C-shaped arm;
a transmission image storage device for saving a transmission image acquired in said image acquisition device;
a judging device which, in accordance with the transmission image from said transmission image storage device, discriminates a region of the pipe that requires image reconstruction for a tomogram or a stereoscopic image; and
an image reconstruction arithmetic device that reconstructs a three-dimensional stereoscopic image by reconstructing a part of the first subject of inspection from a plurality of the transmission image data based on information of the projection part of the first subject of inspection which is a part of the pipe discriminated by said judging device, and by reconstructing a part of the second subject of inspection from a plurality of the transmission image data based on information of the projection part of the second subject of inspection.

2. The X-ray radiation non-destructive inspection system according to claim 1, wherein
said judging device conducts the discrimination by comparing first radiation intensity calculated from an attenuation coefficient and size of the pipe, and second radiation intensity in individual pixels of the transmission image data saved in said transmission image data storage device.

3. The X-ray radiation non-destructive inspection system according to claim 1, wherein
said judging device conducts the discrimination by comparing first radiation intensity calculated from CAD data of the pipe, and second radiation intensity in individual pixels of the transmission image data saved in said transmission image data storage device.

4. The X-ray radiation non-destructive inspection system according to claim 1, wherein
said judging device conducts the discrimination by comparing first radiation intensity derived from a product of the same kind or same lot as the pipe, and second radiation intensity in individual pixels of the transmission image data saved in said transmission image storage device.

5. The X-ray radiation non-destructive inspection system according to claim 4, wherein
said judging device includes input means for designating a spatial region in which the tomogram or stereoscopic image of the transmission image data is to be reconstructed.

6. The X-ray radiation non-destructive inspection system according to claim 4, wherein
said judging device includes a reference data input means for inputting reference data for aid in judging whether the image reconstruction is necessary,
a data comparing means for comparing the reference data and the transmission image data saved in said transmission image storage device, and
a difference judging means for judging existence of a difference based on a comparison result of said data comparing means and a threshold level set by an operator.

7. The X-ray radiation non-destructive inspection system according to claim 1, wherein
said judging device includes input means for designating a spatial region in which the tomogram or stereoscopic image of the transmission image data is to be reconstructed.

8. The X-ray radiation non-destructive inspection system according to claim 1, wherein
said judging device includes a reference data input means for inputting reference data for aid in judging whether the image reconstruction is necessary,
a data comparing means for comparing the reference data and the transmission image data saved in said transmission image storage device, and
a difference judging means for judging existence of a difference based on a comparison result of said data comparing means and a threshold level set by an operator.

9. A pipe inspection method that uses radiation to acquire tomograms or stereoscopic images of a pipe, the method comprising:
a first step for scanning an X-ray radiation source and an X-ray radiation detector side by side along the pipe which is installed in a plant, and for acquiring transmission image data from said X-ray radiation detector, in which the transmission image data include data at a projection part of the first subject of inspection and a projection part of the second subject of inspection which is located at a different depth from the first subject of inspection;
a second step for judging and discriminating a region of the pipe that requires image reconstruction for a tomogram or stereoscopic image based on a plurality of the transmission image data; and
a third step for reconstructing a three-dimensional stereoscopic image by reconstructing a part of the first subject of inspection from a plurality of the transmission image data based on information of the projection part of the first subject of inspection which is a judged part of the pipe, and by reconstructing a part of the second subject of inspection from a plurality of the transmission image data based on information of the projection part of the second subject of inspection, and for inspecting a situation of the pipe.

* * * * *